United States Patent

Venkatesan et al.

Patent Number: 5,294,611
Date of Patent: Mar. 15, 1994

[54] ANGIOTENSIN II RECEPTOR BLOCKING 2,3,6 SUBSTITUTED QUINAZOLINONES

[75] Inventors: Aranapakam M. Venkatesan, Elmhurst; Jeremy I. Levin, Nanuet, both of N.Y.

[73] Assignee: American Cyanamid Company, Wayne, N.J.

[21] Appl. No.: 52,942

[22] Filed: Apr. 23, 1993

[51] Int. Cl.⁵ .............. A61K 31/55; A61K 31/505; C07D 498/04; C07D 498/08
[52] U.S. Cl. .................. 514/211; 514/214; 514/215; 514/228.8; 514/229.2; 514/230.5; 514/258; 514/259; 540/461; 540/476; 540/478; 540/519; 540/520; 540/521; 540/552; 540/578; 544/63; 544/65; 544/66; 544/68; 544/91; 544/92; 544/281; 544/284; 544/287
[58] Field of Search .......... 544/281, 287, 284, 63, 544/65, 66, 68, 91; 514/259, 211, 214, 215, 228.8, 229.2, 230.5, 258; 540/461, 476, 478, 519, 520, 521, 552, 578

[56] References Cited

U.S. PATENT DOCUMENTS 5,162,325 11/1992 Chakravarty et al. ............ 514/259
5,202,322 4/1993 Allen ............................ 514/228.2

FOREIGN PATENT DOCUMENTS 407342 1/1991 European Pat. Off. .
411766 2/1991 European Pat. Off. .
445811 9/1991 European Pat. Off. .
481448 4/1992 European Pat. Off. .
512870 11/1992 European Pat. Off. .

*Primary Examiner*—Emily Bernhardt
*Attorney, Agent, or Firm*—T. S. Szatkowski

[57] ABSTRACT

The invention provides novel 2,3,6 substituted quinazolinones having the formula:

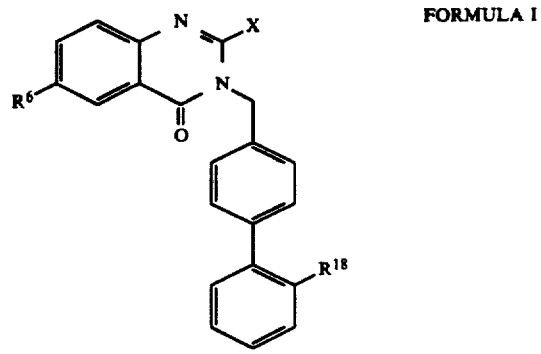

FORMULA I wherein $R^6$, R and X are as described in the specification, which have activity as angiotensin II (AII) antagonists.

49 Claims, No Drawings

ANGIOTENSIN II RECEPTOR BLOCKING 2,3,6 SUBSTITUTED QUINAZOLINONES

BACKGROUND OF THE INVENTION

1. Field of the Invention

This invention relates to certain 2,3,6 substituted quinazolinone compounds which have demonstrated activity as angiotensin II (AII) antagonists and are therefore useful in alleviating angiotensin induced hypertension and for treating congestive heart failure.

SUMMARY OF THE INVENTION

According to the present invention, there are provided novel compounds of Formula I which have angiotensin II antagonizing properties and are useful as hypertensives:

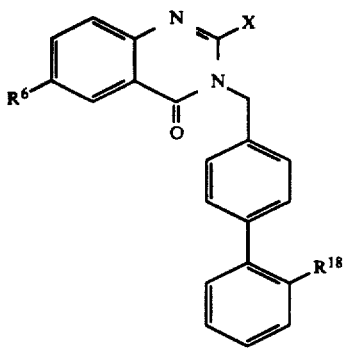

FORMULA I wherein:
R is

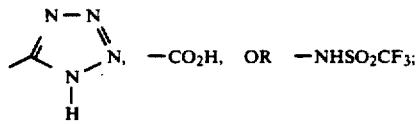

X is lower alkyl of 3 to 5 carbon atoms;
$R^6$ is:

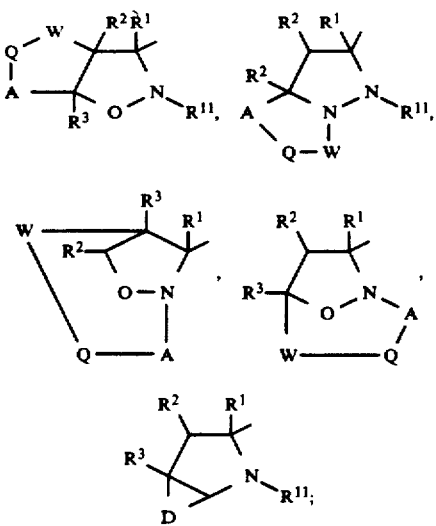

A is $-(CH_2)_n-$;
n is 1, 2, 3, or 4;
W is $-CH_2-$ or

or A and W are each

and are connected by a $-(CH_2)_s-$ bridge, wherein S=1, 2 or 3;
Q is $-O-$, $-CH_2-$ or $$-\underset{\underset{}{|}}{\overset{R^8}{\underset{|}{N}}}-;$$

D is $-(CH_2)_m-$;
m is 3 or 4;
$R^1$ is H, lower alkyl of 1 to 4 carbon atoms (optionally substituted with $-OR^5$, $-CO_2R^5$, $-CN$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridine, thiophene, furan, $-CHO$, $-CO_2R^5$, $-CN$, $$\overset{O}{\underset{}{\overset{\|}{C}}}N(R^5)(R^7) \quad \text{or} \quad \overset{O}{\underset{}{\overset{\|}{C}}}R^5;$$

$R^2$ is H, lower alkyl of 1 to 4 carbon atoms, (optionally substituted with $-OR^5$, $-CO_2R^5$, $-CN$, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridine, thiophene, furan, $-CHO$, $-CO_2R^5$, $-CN$, $$\overset{O}{\underset{}{\overset{\|}{C}}}N(R^5)(R^7) \quad \text{or} \quad \overset{O}{\underset{}{\overset{\|}{C}}}R^5;$$

$R^3$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridine, thiophene, furan, $-OR^5$, $-N(R^5)(R^7)$, $-CO_2R^5$, $-CH_2OR^5$, $-CN$, $-CHO$, $$\overset{O}{\underset{}{\overset{\|}{C}}}N(R^5)(R^7) \quad \text{or} \quad \overset{O}{\underset{}{\overset{\|}{C}}}R^5;$$

$R^5$ is H, lower alkyl of 1 to 4 carbon atoms;
$R^{11}$ is H, lower alkyl of 1 to 4 carbon atoms, cycloalkyl of 5 or 6 carbon atoms, phenyl, substituted phenyl (substitution selected from mono-lower alkyl of 1 to 3 carbon atoms, trifluoromethyl, nitro, O-alkyl of 1 to 3 carbon atoms, P, Cl, or Br), pyridine, thiophene, furan, benzyl, substituted benzyl (substitution selected from mono-lower alkyl of 1 to 3 carbon atoms, trifluoromethyl, nitro, O-alkyl of 1 to 3 carbon atoms, P, Cl, or Br), $-CO_2R^5$, $-SO_2R^{10}$,

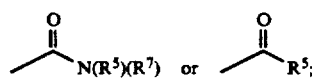

$R^7$ is H, lower alkyl of 1 to 4 carbon atoms;
$R^8$ is H, $-CO_2R^5$, $-SO_2R^{10}$,

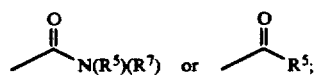

$R^{10}$ is lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br); and pharmaceutically acceptable salts thereof.

The present invention also provides novel intermediate compounds, methods for making the novel 2,3,6 substituted quinazolinone angiotensin II antagonizing compounds, methods of using the novel quinazolinone angiotensin II antagonizing compounds to treat hypertension, congestive heart failure and to antagonize the effects of angiotensin II.

DETAILED DESCRIPTION OF THE INVENTION

The novel compounds of the present invention are prepared according to the following reaction schemes.

Referring to Scheme I, the corresponding anthranilic acid 2 wherein $R^9$ is I, Br or $CH_3$, are heated to reflux in alkyl acid anhydride 3 wherein X is lower alkyl of 3 to 5 carbon atoms to provide the 4H-3,1-benzoxazin-4-ones 4 which are isolated by concentrating the reaction mixtures and used without further purification. When the 4H-3,1-benzoxazin-4-ones 4 are refluxed in ethyl alcohol containing ammonia, or ammonium hydroxide solution, the quinazolinone intermediates 5 are obtained.

Scheme I

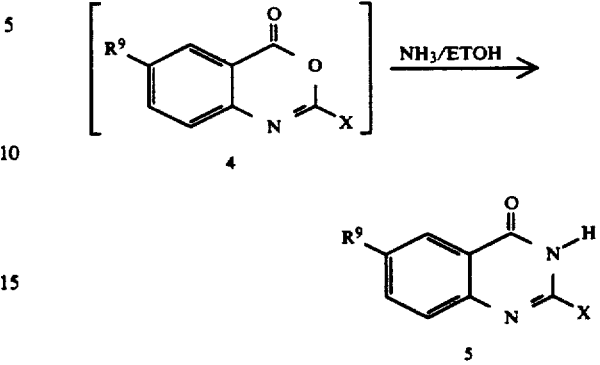

The quinazolinone intermediates 5 are modified according to the following reaction schemes to obtain the novel quinazolinone angiotensin II antagonizing compounds of the present invention.

In Scheme II, 6-methylquinazolinone 6, as prepared by Scheme I, is brominated with N-bromosuccinimide to give the bromomethyl compound 7. Hydrolysis of the bromide with aqueous potassium carbonate in dimethylsulfoxide yields the primary alcohol 8. The alcohol 8 is oxidized with pyridinium dichromate in N,N-dimethylformamide to afford aldehyde 9. The aldehyde 9 is reacted with a variety of Grignard Reagents $R^1MgBr$ or lithium reagents $R^1Li$ in tetrahydrofuran where $R^1$ is hereinbefore defined, with the proviso that for this reaction scheme $R^1$ cannot contain a carbonyl group or be H, $-CO_2R^5$, or

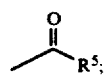

to give the desired secondary alcohol 10. Alcohol 10 is oxidized with pyridinium dichromate in N,N-dimethylformamide to afford ketone 11.

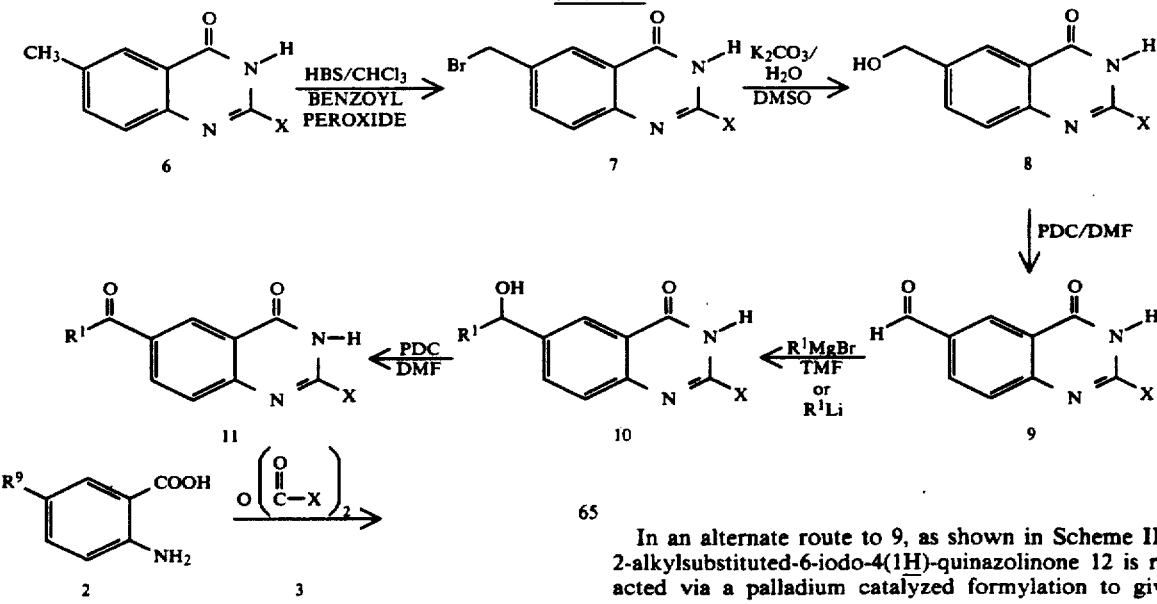

Scheme II

In an alternate route to 9, as shown in Scheme III, 2-alkylsubstituted-6-iodo-4(1H)-quinazolinone 12 is reacted via a palladium catalyzed formylation to give aldehyde 9. Additionally, 12 is converted to ester 13 by palladium (II) catalyzed coupling in the presence of carbon monoxide and methanol. Reduction of 13 with lithium aluminum hydride in tetrahydrofuran gives alcohol 8. Alcohol 8 is oxidized with pyridinium dichromate to yield aldehyde 9.

with sodium hydroxide in water-methanol gives the terminal acetylene 15. Hydration of acetylene is with catalytic mercuric sulfate-sulfuric acid in acetic acid affords methyl ketone 16. The palladium (II) catalyzed coupling of substituted acetylenes where $R^{17}$ is defined as lower alkyl of 1 to 4 carbon atoms with 2-alkylsub-

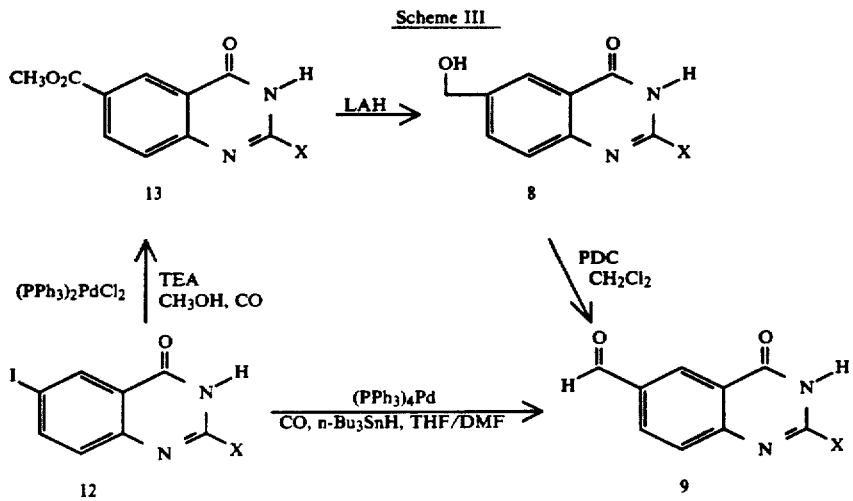

Scheme III

As shown in Scheme IV, the palladium (II) catalyzed coupling of (trimethylsilyl)acetylene with 2-alkylsubstituted-6-iodo-4(1H)-quinazolinone 12 yields the acetylenic quinazolinone 14. Desilylation of the acetylene stituted-6-iodo-4(1H)-quinazolinone 12 yields the acetylenic quinazolinone 17. Hydration of 17 with catalytic mercuric sulfate-sulfuric acid in acetic acid gives ketone 18.

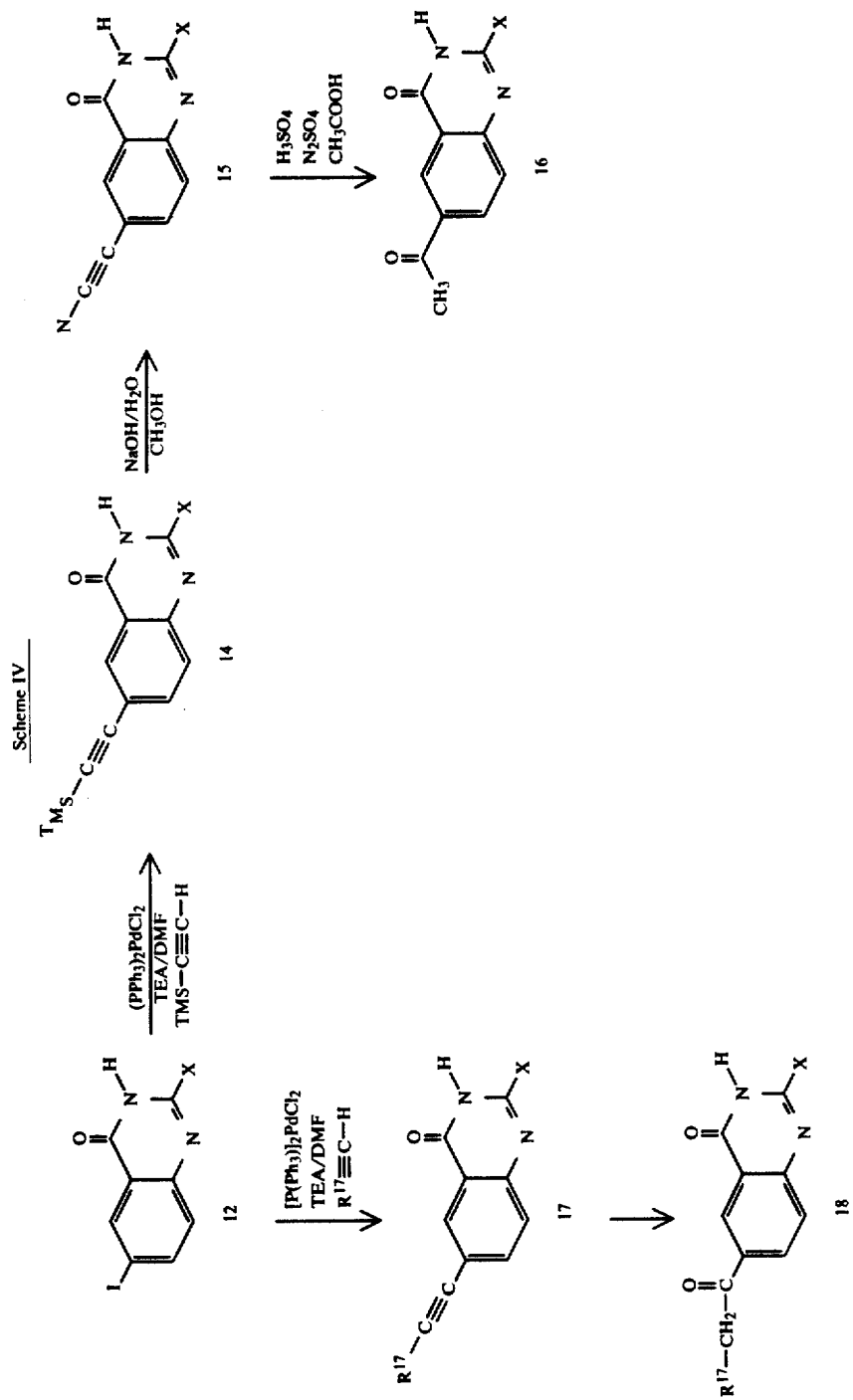

As described in EP 0,497,150, biphenyl 19 is attached to quinazolinone intermediate 11 by initially alkylating the quinazolinone with a para-substituted benzyl bromide and subsequently attaching a second phenyl moiety containing a trityl protected tetrazole or a cyano via a transition metal catalyzed coupling at the para position of the first phenyl ring. Quinazolinone intermediates 16 and 18 are similarly reacted. Alternatively, the coupling of quinazolinone intermediate 11 where X and $R^1$ are hereinbefore defined with biphenyl 19 where $R^{18}$ is a trityl protected tetrazole prepared by the methods of N. B. Mantlo, *J. Chem.*, 34, 2919–2922 (1991) or cyano prepared by the methods outlined in D. J. Carini, *J. Med. Chem.* 34, 2525–2547 (1991) is illustrated in Scheme V and gives coupled product 20 by dissolving 11 and 19 in acetone or another suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium hydride, potassium hydride, sodium methoxide, sodium ethoxide, lithium methoxide, sodium t-butoxide, potassium t-butoxide, lithium diisopropylamide (LDA) or lithium hexamethyldisilazide for 2–48 hours, at 20°–60° C. The obtained alkylated quinazolinone 20 may be purified by chromatography or used as is in further transformations and/or deprotection. Quinazolinone intermediates 16 and 18 are similarly reacted.

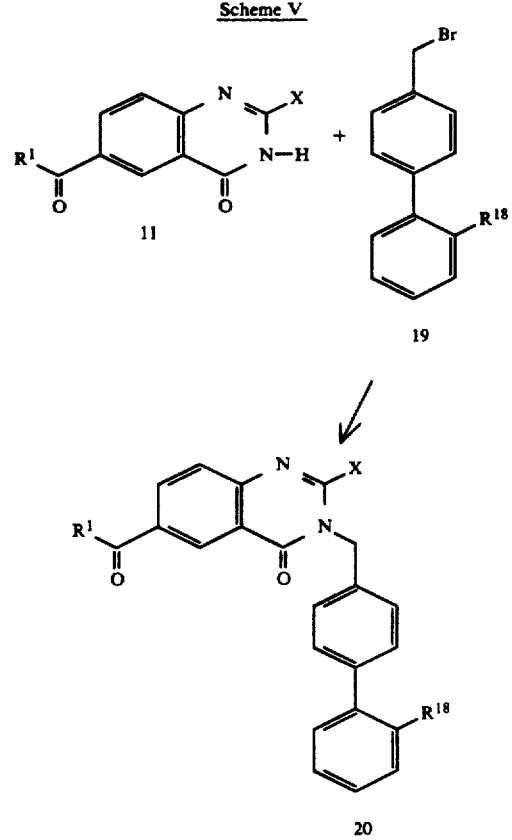

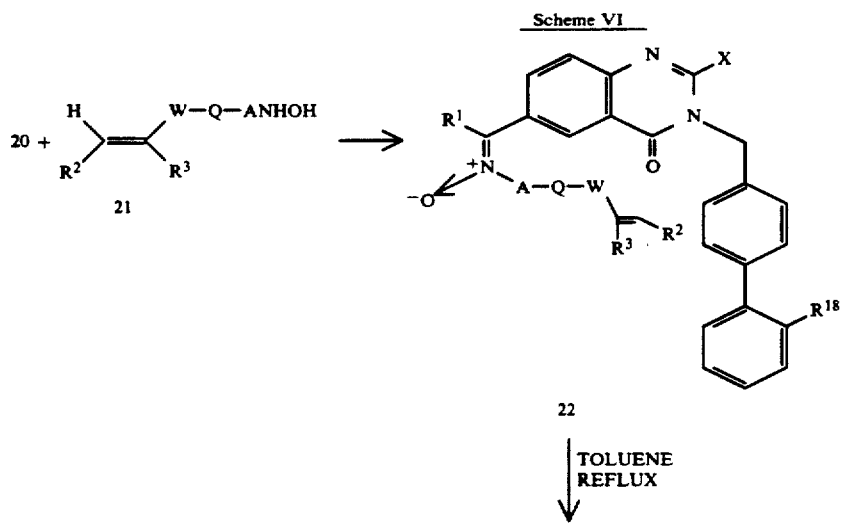

-continued
Scheme VI

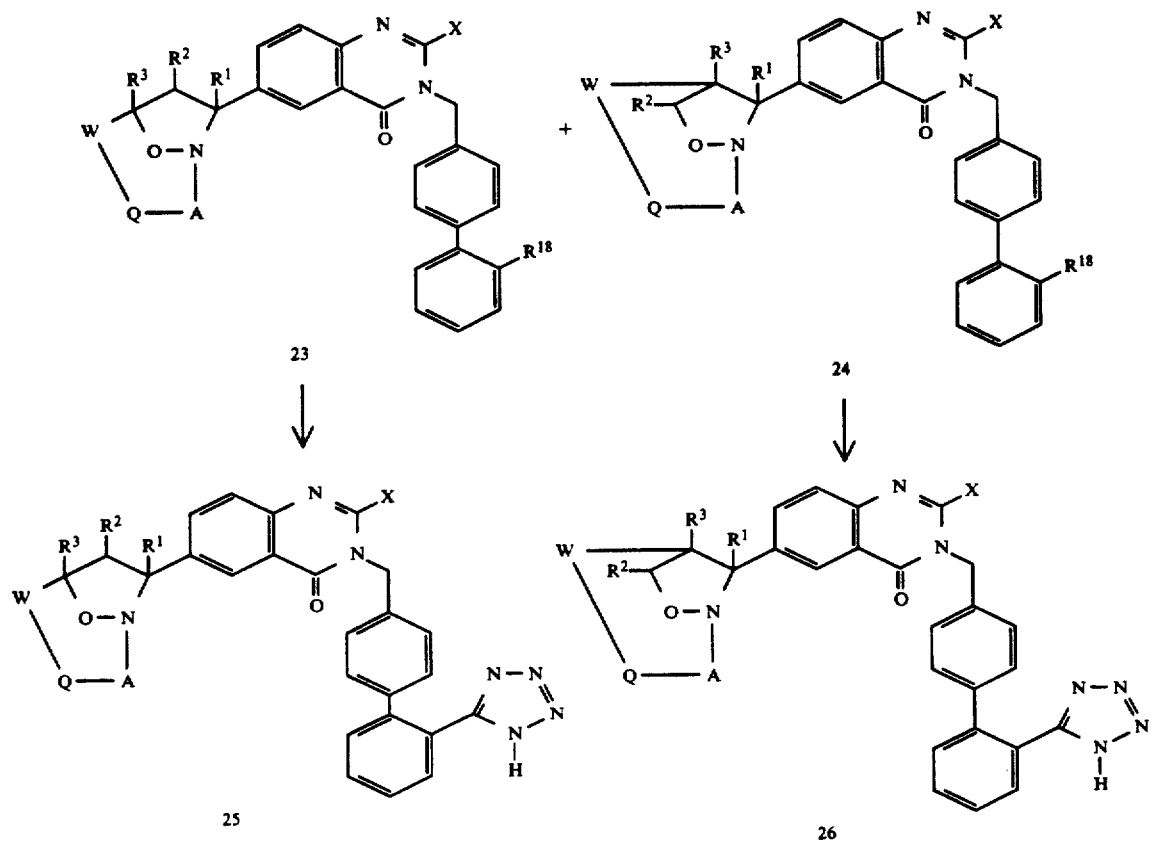

As shown in Scheme VI, aldehyde or ketone 20, where $R^1$ and x are hereinbefore defined, is reacted with an N-substitutedhydroxylamine 21, where $R^2$, $R^3$, W, Q and A are hereinbefore defined prepared by the method of W. Oppolzer et al., Tetrahedron, 41, #17, 3497–3509(1985), at room temperature in chloroform in the presence of molecular sieves to give a nitrone 22. Heating the nitrone 22 at reflux in toluene gives a mixture of bicyclic-substituted quinazolinone 23 and bicyclic-substituted quinazolinone 24.

Reaction of 23 or 24 where $R^{18}$ is cyano with sodium azide in the presence of tri-n-butyltin chloride in refluxing xylene affords the desired tetrazole 25 or 26. Contemplated equivalents to tri-n-butyltin chloride include tri-(loweralkyl $C_1$–$C_4$) tin chlorides and bromides. Contemplated equivalents to sodium azide include potassium azide, and lithium azide. Hydrolysis of 23 or 24 where $R^{18}$ is a trityl protected tetrazole with methanol-tetrahydrofuran at room temperature to reflux or with an aqueous solution containing a catalytic amount of hydrochloric acid or other suitable acid such as sulfuric, trifluoroacetic or hydrogen chloride for 10 minutes to 24 hours at room temperature affords the free tetrazole 25 or 26.

As shown in Scheme VII, aldehyde or ketone 11, where $R^1$ and X are hereinbefore defined is reacted with an N-substitutedhydroxylamine 27 where $R^{11}$ is hereinbefore defined to give nitrone 28. Reaction of 28 with olefin 29 where A, Q, W, $R^2$ and $R^3$ are as defined hereinbefore gives quinazolinone 30.

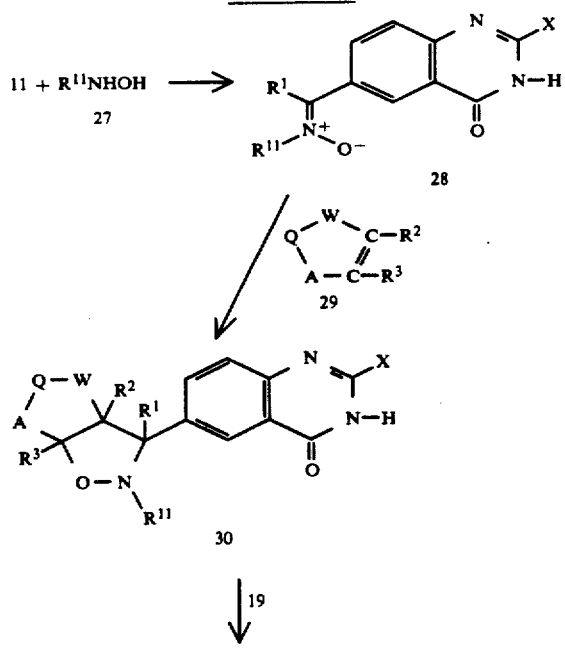

Scheme VII

13
-continued
Scheme VII

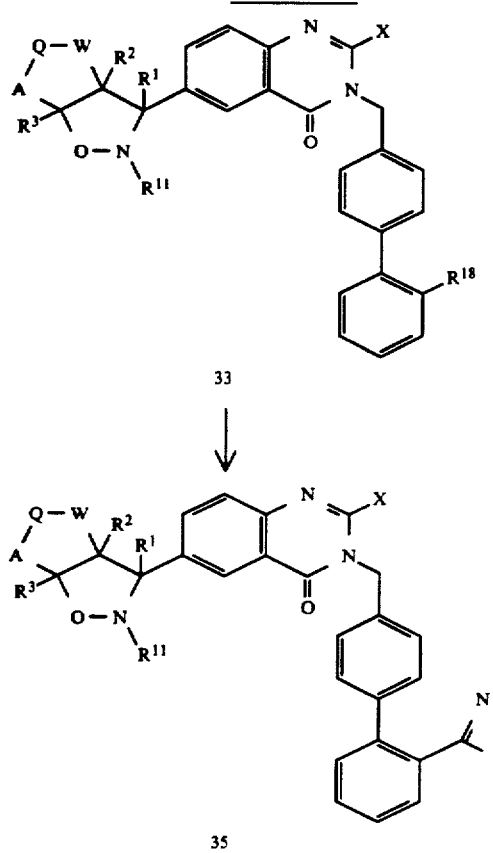

33

Quinazolinone intermediate 30 wherein X, A, Q, W, R$^1$, R$^2$, R$^3$ and R$^{11}$, are hereinbefore defined is coupled with with biphenyl 19 by the methods described hereinabove for scheme V to give coupled product 33. The obtained alkylated quinazolinone 33 may be purified by chromatography or used as is in further transformations and/or deprotection.

Reaction of 33 where R$^{18}$ is cyano with sodium azide in the presence of tri-n-butyltin chloride in refluxing xylene affords the desired tetrazole 35. Contemplated equivalents to tri-n-butyltin chloride include tri-(loweralkyl C$_1$-C$_4$) tin chlorides and bromides. Contemplated equivalents to sodium azide include potassium azide, and lithium azide. Hydrolysis of 33 where R$^{18}$ is a trityl protected tetrazole with methanol-tetrahydrofuran at room temperature to reflux or with an aqueous solution containing a catalytic amount of hydrochloric acid or other suitable acid such as sulfuric, trifluoroacetic or hydrogen chloride for 10 minutes to 24 hours at room temperature affords the free tetrazole 35.

Scheme VIII

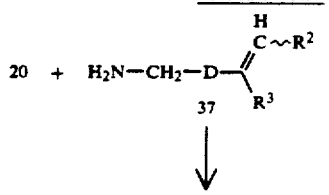

14
-continued
Scheme VIII

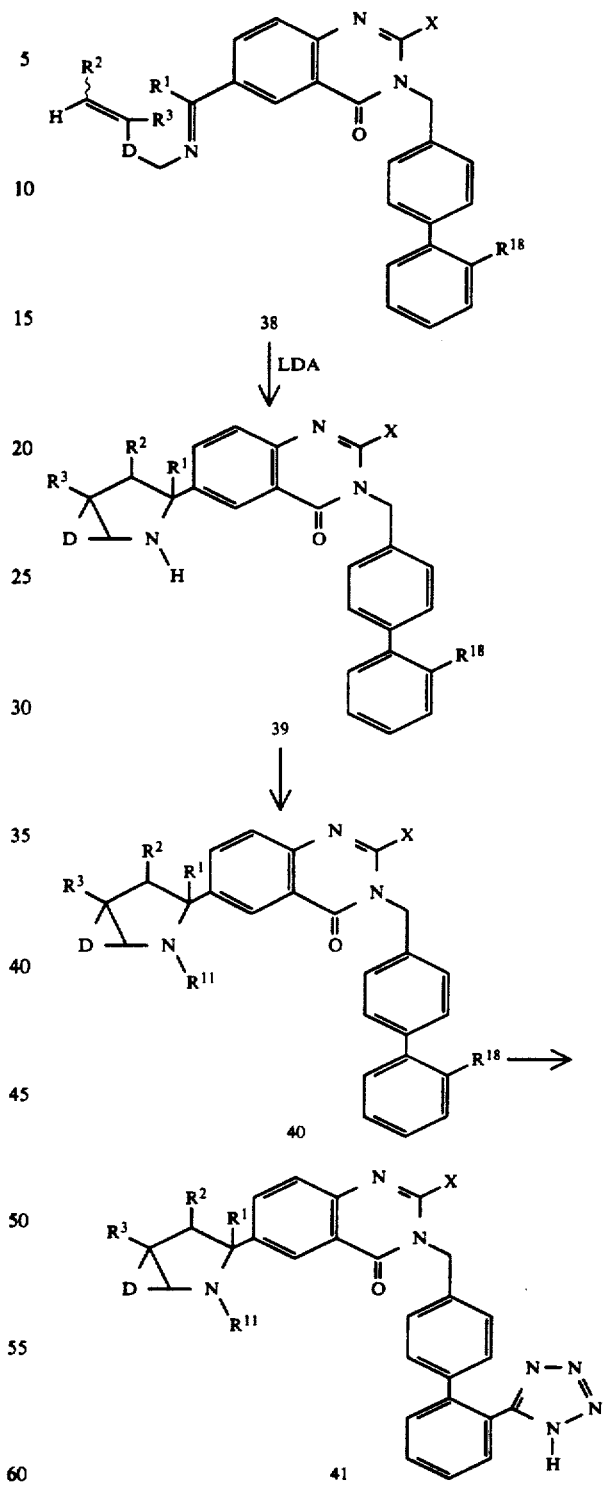

As shown in Scheme VIII, aldehyde or ketone 20, where R$^1$, R$^{18}$ and X are hereinbefore defined is reacted with amine 37 where R$^2$, R$^3$ and D are hereinbefore defined to give quinazolinone intermediate 38. Aza-allyl anion cyclization of 38 with LDA using the method of W. H. Pearson, J. Am. Chem. Soc. 108, 2769–2771 (1986) gives 39 which is converted to substituted intermediate 40 where R[11] is hereinbefore defined. Reaction of 40 where R[18] is cyano with sodium azide in the presence of tri-n-butyltin chloride in refluxing xylene affords the desired tetrazole 41. Contemplated equivalents to sodium azide included potassium azide and lithium azide. Hydrolysis of 40 where R[18] is a trityl protected tetrazole with methanol-tetrahydrofuran at room temperature to reflux or with an aqueous solution containing a catalytic amount of hydrochloric acid or other suitabled acid such as sulfuric, trifluoroacetic or hydrogen chloride for 10 minutes to 24 hours at room temperature affords the free tetrazole 41.

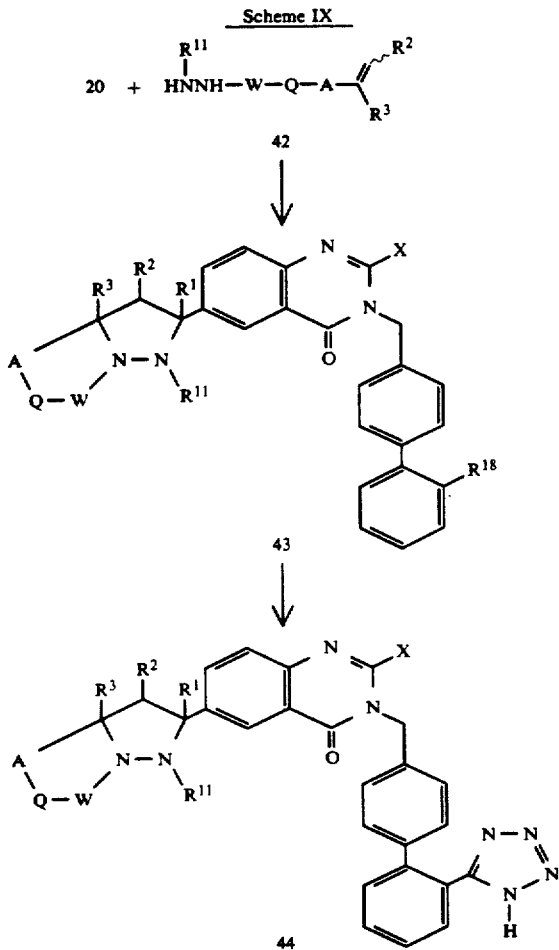

As outlined in Scheme IX, aldehyde or ketone 20, where R[1], R[18] and X are hereinbefore defined is reacted with amine 42, where R[2], R[3], R[11], W, Q and A are hereinbefore defined and cyclized using the method of W. Oppolzer et al., Tet. Lett. 17, 1707-1710 (1972) to give quinazolinone intermediate 43. Reaction of 43 where R[18] is cyano with sodium azide in the presence of tri-n-butyltin chloride in refluxing xylene affords the desired tetrazole 44. Contemplated equivalents to sodium azide include potassium azide and lithium azide. Hydrolysis of 43 where R[18] is a trityl protected tetrazole with methanol-tetrahydrofuran at room temperature to reflux or with an aqueous solution containing a catalytic amount of hydrochloric acid or other suitable acid such as sulfuric, trifluoroacetic or hydrogen chloride for 10 minutes to 24 hours at room temperature affords the free tetrazole 44.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hydroseopicity and solubility. Preferred salts of this invention for the reasons cited above include potassium, sodium, calcium, magnesium and ammonium salts.

Some of the compounds of the hereinbefore described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation are illustrated by the following non-limiting examples.

EXAMPLE 1

2-Butyl-6-(methyl)-4(1H)-quinazolinone

To 20.0 g of 2-amino-5-methylbenzoic acid is added 60 ml of valeric anhydride. The mixture is heated at reflux for 18 hours and then concentrated under reduced pressure. The resulting brown solid residue is dissolved in a mixture of 200 ml of 30% of ammonium hydroxide solution and 300 ml of ethyl alcohol. This mixture is heated at reflux for 5 hours and then allowed to cool to room temperature. After cooling, the precipitate is collected by filtration. The cake is washed with ethanol and water, then dried under vacuum to give 8.92 g of the quinazolinone as a white solid.

CI MASS SPEC MH+ =217.

EXAMPLE 2

2-Butyl-6-iodo-4(1H)-quinazolinone

The method of Example 1 is used with 2-amino-5-iodobenzoic acid to prepare the desired product, m.p. 257°-258° C.

EXAMPLE 3

2-Butyl-6-(bromomethyl)-4(1H)-quinazolinone

To a suspension of 3.50 g of 6-methylquinazolone in 100 ml of chloroform is added 3.39 g of N-bromosuccinimide and 0.25 g of benzoyl peroxide. The reaction mixture is heated at reflux for 18 hours and then filtered hot. A precipitate of 2.21 g of an inseparable mixture of the desired bromide and starting 6-methyl-quinazolinone is obtained and used in Example 4 without further purification.

EXAMPLE 4

2-Butyl-6-(hydroxymethyl)-4(1H)-quinazolinone

To a suspension of 2.0 g of impure 2-butyl-6-(bromomethyl)-4(1H)-quinazolinone (Example 3) in 35 ml of dimethylsulfoxide and 20 ml of water is added 1.0 g of potassium carbonate. The reaction mixture is heated at reflux for 6 hours, resulting in a complete solution. Upon cooling slowly to room temperature a white precipitate forms and is collected by filtration. The filter cake is purified by flash chromatography on silica gel, eluting with 9:1 chloroform-methanol to give 0.67 g of the desired product as a white solid.

CI MASS SPEC 233(M+H).

EXAMPLE 5

2-Butyl-1,4-dihydro-4-oxo-6-quinazolinecarboxaldehyde

To a solution of 0.3 g of 2-butyl-6-(hydroxymethyl)-4(1H)-quinazolinone in 3.5 ml of dry N,N-dimethylformamide is added 1.7 g of pyridinium dichromate. The reaction mixture is stirred at room temperature for 16 hours and then poured into 125 ml of water. The resulting precipitate is removed by filtration and the filtrate extracted with 9:1 chloroform-methanol. The combined organic extracts are dried over magnesium sulfate, filtered and concentrated in vacuo and combined with the precipitate above. The combined solids are purified by flash chromatography on silica gel by eluting with 1:1 ethyl acetate-hexanes to give 0.27 g of the desired product.

CI MASS SPEC 231(M+H).

EXAMPLE 6

2-Butyl-6-(1-hydroxyethyl)-4(1H)-quinazolinone

To a solution of 0.60 g of 2-butyl-1,4-dihydro-4-oxo-6-quinazolinecarboxaldehyde in 30 ml of dry tetrahydrofuran, cooled to 0° C. is added dropwise, 2.61 ml of a 3.0M solution of methylmagnesium bromide in diethyl ether. The reaction is stirred at 0° C. for 30 minutes and then quenched with 10 ml of aqueous ammonium chloride. After diluting with 10 ml of water, the reaction mixture is extracted with 9:1 chloroform-methanol. The combined extracts are dried with magnesium sulfate, filtered and concentrated to yield 0.64 g of the desired product.

CI MASS SPEC 247(MH+).

EXAMPLE 7

2-Butyl-6-(1-hydroxypropyl)-4(1H)-quinazolinone

To a solution of 0.25 g of 2-butyl-1,4-dihydro-4-oxo-6-quinazolinecarboxaldehyde in 10 ml of dry tetrahydrofuran, cooled to a0° C., is added 1.63 ml of 2.0M ethyl magnesium bromide in tetrahydrofuran. The reaction mixture is stirred for 30 minutes at 0° C. and quenched with 20 ml of saturated ammonium chloride solution and 20 ml of water. The reaction mixture is extracted with 9:1 chloroform-methanol, dried over magnesium sulfate, filtered and evaporated in vacuo to give 0.26 g of the desired product.

CI MASS SPEC 261(MH+).

EXAMPLE 8

2-Butyl-1,4-dihydro-4-oxo-6-quinazolinecarboxaldehyde

To a solution of 1.0 g of 2-butyl-6-iodo-4(1H)-quinazolinone and 0.355 g of tetrakis(triphenylphosphine)palladium in 15 ml of tetrahydrofuran and 5 ml of N,N-dimethylformamide, heated to 55° C. under an atmosphere of carbon monoxide is added a solution of 1.40 g of tri-n-butyltin hydride in 2.5 ml of toluene over 6 hours via a syringe pump. After the addition is complete the reaction is allowed to cool to room temperature, diluted with brine and extracted with chloroform. The combined organics are concentrated in vacuo and the resulting residue triturated with ether. The precipitate is collected by filtration and purified by flash chromatography on silica gel, eluting with 1:1 ethyl acetate-hexanes to give 0.35 g of the desired product, m.p. 242°-244° C.

EXAMPLE 9

2-Butyl-6-[(trimethylsilyl)ethylnyl]-4(1H)-quinazolinone

To a solution of 1.0 g of 2-butyl-6-iodo-4(1H)-quinazolinone 0.043 g of bis(triphenylphosphine) palladium (II) chloride and 5.8 mg of copper (I) iodide in 5.0 ml of N,N-dimethylformamide and 5.0 ml of triethylamine is added 0.36 g of (trimethylsilyl) acetylene. The resulting reaction mixture is heated at 45° C. for 1 hour and then 65° C. for 5 hours. Upon cooling, the reaction mixture is concentrated in vacuo and the residue purified by flash chromatography on silica gel, eluting with 1:3 ethyl acetate-hexane to yield 0.75 g of the desired product as a white solid.

CI MASS SPEC 299(MH+).

EXAMPLE 10

2-Butyl-6-ethylnyl-4(1H)-quinazolinone

To a solution of 0.70 g of 2-butyl-6-[(trimethylsilyl)ethynyl]-4(1H)-quinazolinone in 20 ml of methanol and 20 ml of tetrahydrofuran is added 10.0 ml of 1.0N sodium hydroxide solution. The reaction is stirred at room temperature for 2 hours and then diluted with 5% hydrochloric acid solution until the pH is 2. The resulting tan precipitate is collected by filtration and dried in vacuo to yield 0.50 g of the desired product.

CI MASS SPEC 227(MH+).

EXAMPLE 11

6-Acetyl-2-butyl-4(1H)-quinazolinone

To a solution of 1.20 g of 2-butyl-6-ethynyl-4(1H)-quinazolinone in 90 ml of acetic acid is added 0.45 g of mercuric sulfate, 0.9 ml of water and 0.3 ml of sulfuric acid. The reaction mixture is heated at reflux for 5 hours, cooled to room temperature and quenched with 150 ml of water. The resulting mixture is concentrated in vacuo, diluted with 150 ml of water and extracted with 6:1 chloroform-methanol. The combined organics are dried over magnesium sulfate, filtered and concentrated in vacuo. The residue is purified by flash chromatography on silica gel, eluting with 1:1 ethyl acetate-hexanes to give 0.67 g of the desired product as a white solid.

CI MASS SPEC 245(MH+).

EXAMPLE 12

2-Butyl-6-(hydroxyphenylmethyl)-4(1H)-quinazolinone

To a stirred solution of 2.00 g of 2-butyl-1,4-dihydro-4-oxo-6-quinazolinecarboxaldehyde in 100 ml of tetrahydrofuran, cooled at 0° C., is added 13.0 ml of 2.0M phenyllithium and stirring continued is for 1 hour. The cooling is removed and the reaction allowed to reach room-temperature followed by an additional 30 minutes at room temperature. The reaction is diluted with saturated ammonium chloride solution and extracted with ethyl acetate. The organic layer is dried, evaporated to a residue, which is purified by chromatography on silica gel by elution with 0.25:100 methanol-chloroform to give 0.932 g of the desired product.

CI MASS SPEC 309(MH+).

EXAMPLE 13

Methyl 2-butyl-1,4-dihydro-4-oxo-6-quinazolinecarboxylate

To a solution of 1.00 g of 2-butyl-6-iodo-4(1H)-quinazolinone and 6.0 ml of triethylamine in 25 ml of methanol and 5 ml of N,N-dimethylformamide is added 0.275 g of bis-(triphenylphosphine)palladium (II) chloride. The reaction mixture is heated at reflux under an atmosphere of carbon monoxide for 16 hours, then allowed to cool and concentrated in vacuo. The residue is purified by flash chromatography on silica gel, eluting with 1:1 ethyl acetate-hexanes to give 0.389 g of the desired product as a white solid.

CI MASS SPEC 261(MH+).

EXAMPLE 14

2-Butyl-6-(hydroxymethyl)-4(1H)-quinazolinone

To a suspension of 0.013 g of lithium aluminum hydride in 5.0 ml of tetrahydrofuran is added 0.100 g of methyl 2-butyl-1,4-dihydro-4-oxo-6-quinazolinecarboxylate followed by stirring at room temperature for 5 hours. An additional 20 mg of lithium aluminum hydride is added and stirring continued for 18 hours. An additional 20 mg of lithium aluminum hydride is added and stirring continued for an additional 8 hours. The reaction mixture is poured into 75 ml of water and extracted with ethyl acetate. The extract is evaporated in vacuo to a residue which is stirred with acetone and filtered to give 0.040 g of the desired product as a white solid.

CI MASS SPEC 233 (MH+).

EXAMPLE 15

2-Butyl-6-(hydroxymethyl)-3-[[2'-[1-(triphenylmethyl)-1H-tetrazol-5-yl][1,1'-biphenyl]-4-yl]methyl-4(3H)-quinazolinone A mixture of 0.198 g of 2-butyl-6-(hydroxymethyl)-4(1H)-quinazolinone, 0.477 g of 5-[4'-(bromomethyl)[1,1'-biphenyl]-2-yl]-1-(triphenylmethyl)-1H-tetrazole and 0.500 g of potassium carbonate in 15.0 ml of dry acetone is heated at reflux for 18 hours. The reaction mixture is allowed to cool to room temperature and evaporated to a residue. The residue is diluted with water and extracted with chloroform. The organic layer is washed with brine, dried with Na2SO4 and evaporated in vacuo to a residue which is purified on thick layer silica gel chromatography plates using 1:1 ethyl acetate-hexanes to give 0.14 g of the desired product. FAB MASS SPEC 709 (M+H).

EXAMPLE 16

2-Butyl-3,4-dihydro-4-oxo-3-[[2'-[1-(triphenylmethyl)-1H-tetrazol-5-yl][1,1'-biphenyl]-4-yl]methyl]-6-quinazolinecarboxaldehyde A mixture of 6.48 g of 2-Butyl-6-(hydroxymethyl)-3-[[2'-[1-(triphenylmethyl)-1H-tetrazol-5-yl][1,1'-biphenyl]-4-yl]methyl-4(3H)quinazolinone and 5.16 g of pyridinium dichromate in 20 ml of methylene chloride is stirred at room temperature for 18 hours. The reaction mixture is diluted with 100 ml of ether and filtered through a short pad of MGSO4. The filtrate is concentrated in vacuo to give the desired product as a residue. FAB MASS SPEC 729 (M+Na).

EXAMPLE 17

2-Butyl-6-(9-oxa-1-azabicyclo[4.2.1]non-8-yl)-3-[[2'-[1-(triphenylmethyl)-1H-tetrazol-5-yl][1,1'-biphenyl]-4-yl]methyl-4(3H)-quinazolinone A mixture of 0.198 g of 2-Butyl-3,4-dihydro-4-oxo-3-[[2'-[1-(triphenylmethyl)-1H-tetrazol-5-yl][1,1'-biphenyl]-4-yl]methyl]-6-quinazolinecarboxaldehyde and 0.034 g of N-(5-hexenyl)hydroxylamine in 5.0 ml of toluene is heated at reflux for 18 hours then concentrated in vacuo to a residue. The residue is purified by column chromatography on silica gel using 1:1 ethyl acetate-hexanes to give 47 mg of the desired product.

EXAMPLE 18 cis-2-Butyl-6-(9-oxa-1-azabicyclo[4.2.1]non-8-yl)-3-[[2'-(1H-tetrazol-5-yl)[1,1'-biphenyl]-4-yl-methyl-4(3H)-quinazolinone A mixture of 0.154 g of 2-Butyl-6-(9-oxa-1-azabicyclo[4.2.1]non-8-yl)-3-[[2'-[1-(triphenylmethyl)-1H-tetrazol-5-yl][1,1'-biphenyl]-4-yl]methyl-4(3H)-quinazolinone in 5.0 ml of methanol and 1.0 ml of tetrahydrofuran is heated at reflux for 18 hours. The volatiles are evaporated in vacuo to give 0.053 g of the desired product. FAB MASS SPEC 562 (M+H).

EXAMPLE 19

2-Butyl-6-(7-oxa-1-azabicyclo[3.2.1]-oct-8-yl)-3-[[2'-[1-(triphenylmethyl))-1H-tetrazol-5-yl][1,1'-biphenyl]-4-yl]methyl]-4(3H)-quinazolinone

EXAMPLE 20

2-Butyl-6-(8-oxa-1-azabicyclo[3.2.1]oct-7-yl)-3-[[2'-[1-(triphenylmethyl)-1H-tetrazol-5-yl][1,1'-biphenyl]-4-yl]methyl]-4(3H)-quinazolinone A mixture of 0.487 g of N-(4-pentenyl)hydroxylamine oxalate and 20 ml of 6N KOH is stirred and extracted with ether. The organic layer is separated and dried with solid NAOH. The organic layer is separated and combined with 0.900 g of 2-butyl-3,4-dihydro-4-oxo-3-[[2'-[1-(triphenylmethyl)-1H-tetrazol-5-yl][1,1'- biphenyl]-4-yl]methyl]-6-quinazolinecarboxaldehyde and the volatiles concentrated in vacuo to a residue which is dissolved in CHCl₃ and 4A molecular sieves added. The reaction mixture is stirred overnight at room temperature and filtered. The filtrate is evaporated in vacuo to a residue which is purified by column chromatography on silica gel using 1:1 ethyl acetate-hexanes to all ethyl acetate to afford 0.716 g of residue which is dissolved in 30 ml of toluene and heated at reflux for 12 hours. The volatiles are evaporated in vacuo to afford a residue which is purified by high pressure liquid chromatography on silica gel using 1:2 ethyl acetate-hexanes to give 0.134 g of the first desired product as a pale yellow foam and 2 mg of the second desired product as a yellow glass. FAB MASS SPEC 812 (M+Na).

EXAMPLE 21

2-Butyl-6-(7-oxa-1-azabicyclo[3.2.1]oct-8-yl)-3-[[2'-(1H-tetrazol-5-yl)[1,1'-biphenyl]-4-yl]-methyl-4(3H)-quinazolinone A mixture of 0.124 g of 2-butyl-6-(7-oxa-1-azabicyclo[3.2.1]oct-8-yl)-3-[[2'-[1-(triphenylmethyl)-1H-tetrazol-5-yl][1,1'-biphenyl]-4-yl]methyl-4(3H)-quinazolinone in 5.0 ml of methanol and 1.0 ml of tetrahydrofuran is heated at reflux for 16 hours, cooled and concentrated in vacuo to a residue which is purified by column chromatography on silica gel using 9:1 chloroform-methanol to give 0.073 g of the desired product as a white solid. FAB MASS SPEC 548 (M+H).

EXAMPLE 22

2-Butyl-6-[(methylimino)methyl]-4(1H)-quinazolinone N⁶-oxide

To a stirred solution of 2.7 g of sodium methoxide in 50 ml of ethyl alcohol, cooled to 0° C. is added 4.1 g of N-methylhydroxylamine hydrochloride. After stirring for 10 minutes, 2.3 g of 2-butyl-1,4-dihydro-4-oxo-6-quinazolinecarboxaldehyde is rapidly added. The cooling bath is removed and the reaction mixture stirred at room temperature for 18 hours. The volatiles are evaporated in vauco to a yellow solid residue which is stirred with water, filtered, the cake washed with water and air dried to afford 2.3 g of the desired product as a yellow solid, m.p. 206° C.

EXAMPLE 23

2-Butyl-6-[[(phenylmethyl)imino]methyl]-4(1H)-quinazolinone N⁶-oxide

This reaction is performed under the same conditions as Example 22 using 2.3 g of 2-butyl-1,4-dihydro-4-oxo-6-quinazolinecarboxaldehyde, 1.2 g of sodium methoxide, 25 ml of ethyl alcohol and 3.18 g of N-benzylhydroxylamine hydrochloride to give 2.9 g of the desired product as a yellow solid, m.p. 180° C.

EXAMPLE 24

2-Butyl-6-[(cyclohexylimino)methyl]-4(1H)-quinazolinone N⁶-oxide

This reaction is performed under the same conditions as Example 22 using 4.0 g of 2-butyl-1,4-dihydro-4-oxo-6-quinazoline carboxaldehyde, 2.65 g of sodium methoxide, 150 ml of ethyl alcohol and 7.55 g of N-cyclohexylhydroxylamine hydrochloride to give 4.2 g of the desired product as a yellow solid. Mass Spec (EI) 327.

EXAMPLE 25

(3α,3aα,6aα) -2-butyl-6-(hexahydro-2-methyl-4-oxo-2H-cyclopent[d]isoxazol-3-yl-4(1H)-quinazolinone A mixture of 1.0 g of 2-butyl-6-[(methylimino)methyl]-4(1H)-quinazolinone N⁶-oxide and 2 ml of 2-cyclopenten-3-one in 15 ml of toluene is heated at reflux for 8 hours then allowed to cool. The volatiles are evaporated in vacuo to give a residue which is purified by chromatography on silica gel using 60% ethyl acetate-hexanes to give 1.1 g of the desired product as a yellow solid, m.p. 182° C.

Examples 26-36 in Table I are prepared under substantially the same conditions as Example 25 from the appropriately substituted hydroxylamine, quinazolinone N⁶-oxide and olefin starting materials.

TABLE I

| Ex. No. | R⁶ | X | Starting Olefin | Starting RNHOH.HCl R | Reaction Time (Hours) | m.p. °C. or Mass Spec. |
|---|---|---|---|---|---|---|
| 26 | | —(CH₂)₃CH₃ | Cis-cyclo-octene | CH₃— | 48 | 167° |

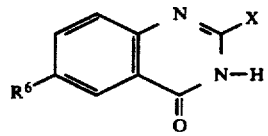

TABLE I-continued
| Ex. No. | R[6] | X | Starting Olefin | Starting RNHOH.HCl R | Reaction Time (Hours) | m.p. °C. or Mass Spec. |
|---|---|---|---|---|---|---|
| 27 | 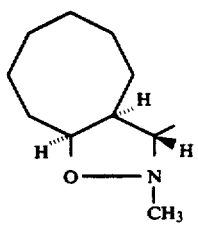 | —(CH$_2$)$_3$CH$_3$ | Cis-cyclo-octene | CH$_3$— | 48 | 176–180° |
| 28 | 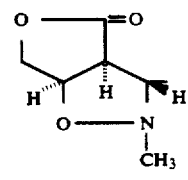 | —(CH$_2$)$_3$CH$_3$ | 2(5H)-furanone | CH$_3$— | 24 | 190–193° |
| 29 | 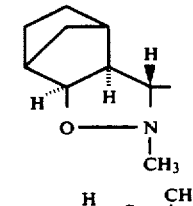 | —(CH$_2$)$_3$CH$_3$ | Norbornylene | CH$_3$— | 24 | 166° |
| 30 | 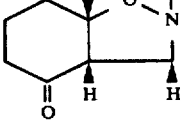 | —(CH$_2$)$_3$CH$_3$ | 1-cyclohexene-3-one | CH$_3$— | 48 | 186° |
| 31 | 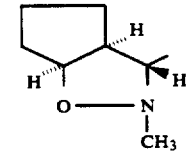 | —(CH$_2$)$_3$CH$_3$ | cyclopentene | CH$_3$— | 48 | 147–149° |
| 32 | 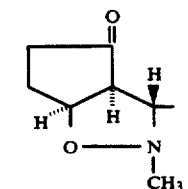 | —(CH$_2$)$_3$CH$_3$ | 1-cyclopentene-3-one | CH$_3$— | 8 | 182° |
| 33 | 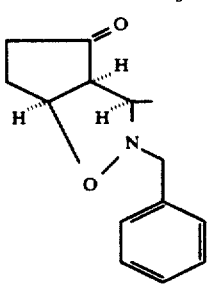 | —(CH$_2$)$_3$CH$_3$ | 1-cyclopentene-3-one | PhCH$_2$— | 24 | 418(M + H) |

TABLE I-continued

| Ex. No. | R⁶ | X | Starting Olefin | Starting RNHOH.HCl R | Reaction Time (Hours) | m.p. °C. or Mass Spec. |
|---|---|---|---|---|---|---|
| 34 | (cyclopentanone-fused bicyclic with N-O-CH2Ph) | —(CH$_2$)$_3$CH$_3$ | 1-cyclopentene-3-one | PhCH$_2$— | 24 | 418(M + H) |
| 35 | (furanone-fused bicyclic with O—N-CH2Ph) | —(CH$_2$)$_3$CH$_3$ | 2(5H)-furanone | PhCH$_2$— | 24 | 176° |
| 36 | (furanone-fused bicyclic with O—N-CH2Ph) | —(CH$_2$)$_3$CH$_3$ | 2(5H)-furanone | PhCH$_2$— | 24 | 151° |

EXAMPLES 37 AND 38

(3α,3aα,6aα)-2-butyl-6-(hexahydro-2-methyl-4-oxofuro[3,4-d]isoxazol-3-yl)-3-[[2'-[1-(triphenylmethyl)-1H-tetrazol-5-yl][1,1'-biphenyl]-4-yl]methyl]-4(3H)-quinazolinone and (3α,3aα,6aα)
-2-butyl-6-(hexahydro-2-methyl-4-oxofuro[3,4-d]isoxazol-3-yl)-3-[[2'-[1-(triphenylmethyl)-1H-tetrazol-5-yl][1,1'-biphenyl]-4-yl]methyl]-4(3H)-quinazolinone isomer 2

A mixture of 343 mg of (3α,3aα,6aα)-2-butyl-6-(hexahydro-2-methyl-4-oxofuro[3,4-d]isoxazol-3-yl)-4(1H)-quinazolinone, 552 mg of 5-[4'-(bromomethyl)[1,1'-biphenyl]-2-yl]-1-(triphenylmethyl)-1H-tetrazole and 2 g of K$_2$CO$_3$ in 200 ml of acetone is heated at reflux for 24 hours. The reaction mixture is filtered and the filtrate evaporated in vacuo to a residue which is purified by column chromatography on silica gel by elution with 30% ethyl acetate-hexanes to give 400 mg of the first desired product as a solid and 250 mg of the second desired product as a solid.

Examples 39-47 in Table II are prepared under substantially the same conditions as Examples 37 and 38 from the appropriately substituted quinazolinone starting materials.

TABLE II

| Ex. No. | R⁶ | X | Ex. No. S. Material | m.p. °C. or Mass Spec. |
|---|---|---|---|---|
| 39 | (cyclopentyl-fused isoxazoline, N-CH₃) | —(CH₂)₃CH₃ | 31 | 803 (M + H) |
| 40 | (norbornyl-fused isoxazoline, N-CH₃) | —(CH₂)₃CH₃ | 29 | 829 (M + H) |
| 41 | (cyclohexanone-fused isoxazoline, N-CH₃) | —(CH₂)₃CH₃ | 30 | 831 (M + H) |
| 42 | (cyclooctyl-fused isoxazoline, N-CH₃) | —(CH₂)₃CH₃ | 27 | 846 (M + H) |
| 43 | (cyclopentanone-fused isoxazoline, N-CH₃) | —(CH₂)₃CH₃ | 32 | 893 (M + H) |
| 44 | (cyclopentanone-fused isoxazoline, N-CH₂Ph) | —(CH₂)₃CH₃ | 33 | 894 (M + H) |
| 45 | (bicyclic oxo-isoxazoline, N-CH₂Ph) | —(CH₂)₃CH₃ | 36 | 895 (M + H) |
| 46 | (bicyclic oxo-isoxazoline, N-CH₂Ph) | —(CH₂)₃CH₃ | 35 | 895 (M + H) |
| 47 | (cyclopentanone-fused isoxazoline, N-CH₂Ph) | —(CH₂)₃CH₃ | 34 | 893 (M + H) |

EXAMPLE 48

(3α,3aα,6aα)-2-butyl-6-(hexahydro-2-methyl-4-oxo-2H-cyclopent[d]-isoxazol-3-yl)-3-[[2'-(1H-tetrazol-5-yl)[1,1'-biphenyl]-4-yl]methyl-4(3H)-quinazolinone A mixture of 250 mg of (3α,3aα,6aα)-2-butyl-6-(hexahydro-2-methyl-2H-cyclopent[d]-isoxazol-3-yl)-3-[[2'-[1-(triphenylmethyl)-1H-tetrazol-5-yl][1,1'-biphenyl]-4-yl]methyl]-4(3H)-quinazolinone in 50 ml of 1:1 tetrahydrofuran-methanol is heated at reflux for 18 hours. The volatiles are evaporated in vacuo and the residue is purified by chromatography on silica gel thick layer plates using a solvent system of 60:20:20:5 ethyl acetate-hexanes-chloroform-methanol to give 110 mg of the desired product. m.p. 118° C.

Examples 49–57 in Table III are prepared under substantially the same conditions as Example 48 from the appropriately substituted quinazolinone starting materials.

TABLE III

[Structure: R⁶-substituted benzene with N=C(X)-N(CH₂-biphenyl-tetrazole)-C(=O) core]

| Ex. No. | R⁶ | X | Ex. No. S. Material | m.p. °C. or Mass Spec. |
|---|---|---|---|---|
| 49 | cyclohexanone with O—N—CH₃ oxime ether substituent | —(CH₂)₃CH₃ | 41 | 126° |
| 50 | cyclopentane with O—N—CH₃ substituent | —(CH₂)₃CH₃ | 39 | 562 (M + H) |
| 51 | bicyclic with O—N—CH₃ substituent | —(CH₂)₃CH₃ | 40 | 86° |
| 52 | cyclooctane with O—N—CH₃ substituent | —(CH₂)₃CH₃ | 42 | 603 (M + H) |
| 53 | lactone with O—N—CH₃ substituent | —(CH₂)₃CH₃ | 38 | 160–165° |
| 54 | lactone with O—N—CH₃ substituent | —(CH₂)₃CH₃ | 37 | 150° |

TABLE III-continued

| Ex. No. | R⁶ | X | Ex. No. S. Material | m.p. °C. or Mass Spec. |
|---|---|---|---|---|
| 55 | cyclopentanone with O—N—benzyl substituent | —(CH₂)₃CH₃ | 47 | 99° |
| 56 | lactone with O—N—benzyl substituent | —(CH₂)₃CH₃ | 46 | 138° |
| 57 | lactone with O—N—benzyl substituent | —(CH₂)₃CH₃ | 45 | 149° |

Angiotensin II Antagonists In Vitro Tests

Materials and Methods

Beef adrenals are obtained from a local slaughter house (maxwell-Cohen). [¹²⁵I](Sar¹,Ile⁸)AngII, S.A. 2200 Ci/mmole, is purchased from Dupont (NEN®, Boston, Mass.). All unlabeled AngII analogs, Dimethylsulfoxide (DMSO), nucleotides, bovine serum albumin (BSA) are purchased from Sigma Chemical Co., St. Louis, Mo. U.S.A.

Preparation of Membranes

Approximately sixteen (16) to twenty (20) beef adrenal glands are processed as follows: fresh adrenal glands received on crushed ice are cleaned of fatty tissues and the tough membranes encapsulating the glands are removed and discarded. The brownish tissue forming the adrenal cortex is scraped off and finely minced with scissors before homogenization. Care is taken to avoid contamination with medullary tissue during dissection. The scraped cortices are suspended in twenty volumes of an ice-cold buffer medium consisting of 10 mM Tris.HCl (pH 7.4 at 22° C.) and containing 1.0 mM EDTA and 0.2M sucrose. Unless otherwise indicated, all subsequent operations are done at 4° C. The tissue is homogenized in a glass homogenizer with a motor-driven teflon pestle with a clearance of 1.0 mm. The homogenate is centrifuged first at low speed (3,000× g) for 10 min. The resulting pellet is discarded and the supernatant fluid recentrifuged at 10,000× g for 15 minutes to give a $P_2$ pellet. This $P_2$ pellet is discarded and the liquid phase is carefully decanted off in clean centrifuge tubes and recentrifuged at high speed (100,000× g) for 60 min. The translucent final pellet is harvested and combined in a small volume (20–50.0 ml) of 50.0 mM Tris.HCl buffer, pH 7.2. A 100 ul aliquot is withdrawn and the protein content of the preparation is determined by the Lowry's method (Lowry, O. H., Rosebrough, N. F., Parr, A. L. and Randall, R. J., Protein measurement with Folin phenol reagent. J. Biol. Chem., 48, 265–275; 1951). The pelleted membrane is reconstituted in 50.0 mM Tris.HCl buffer containing 0.1 mM of phenylmethylsulfonyl fluoride (PMSF) to give approximately a protein concentration of 2.5 mg per ml of tissue suspension. The membrane preparation is finally aliquoted in 1.0 ml volumes and stored at −70° C. until use in the binding assays.

Receptor Binding Assay

Binding of [$^{125}$I](Sar$^1$,Ile$^8$)AngII

The binding of [$^{125}$I](Sar$^1$,Ile$^8$)AngII to microsomal membranes is initiated by the addition of reconstituted membranes (1:10 vols.) in freshly made 50.0 mM Tris.HCl buffer, pH 7.4 containing 0.25% heat inactivated bovine serum albumin (BSA): 80 ul membrane protein (10 to 20 ug/assay) to wells already containing 100 ul of incubation buffer (as described above) and 20 ul [$^{125}$I](Sar$^1$,ILE$^8$)AngII (Specific Activity, 2200 Ci/mmole). Non-specific binding is measured in the presence of 1.0 uM unlabeled (Sar$^1$,ILE$^8$)AngII, added in 20 ul volume. Specific binding for [$^{125}$I](Sar$^1$,Ile$^8$) AngII is greater than 90%. In competition studies, experimental compounds are diluted in dimethylsulfoxide (DMSO) and added in 20 ul to wells before the introduction of tissue membranes. This concentration of DMSO is found to have no negative effects on the binding of [$^{125}$I] (Sar$^1$,Ile$^8$) AngII to the membranes. Assays are performed in triplicate. The wells are left undisturbed for 60 min. at room temperature. Following incubation, all wells are harvested at once with a Brandel ® Harvester especially designed for a 96 well plate (Brandel ® Biomedical Research & Development Labs. Inc., Gaithersburg, Md., U.S.A.). The filter discs are washed with 10×1.0 ml of cold 0.9% NaCl to remove unbound ligand. Presoaking the filter sheet in 0.1% polyethyleneimine in normal saline (PEI/Saline) greatly reduces the radioactivity retained by the filter blanks. This method is routinely used. The filters are removed from the filter grid and counted in a Parkard ® Cobra Gamma Counter for 1 min. (Packard Instrument Co., Downers Grove, Ill., U.S.A.). The binding data are analyzed by the non-linear interactive "LUNDON-1" program (LUNDON SOFTWARE Inc., Cleveland, Ohio U.S.A.). Compounds that displace 50% of the labelled angiotensin II at the screening dose of 50 μM are considered active compounds and are then evaluated in concentration-response experiments to determine their $IC_{50}$ values. The results are shown in Table IV.

TABLE IV

| Ex. No. | R$^6$ | X | Angiotensin II Receptor Binding $IC_{50}$(M) |
|---|---|---|---|
| 18 | H (bicyclic ether-amine) | —(CH$_2$)$_3$CH$_3$ | 4.2 × 10$^{-8}$ |
| 21 | (bicyclic ether-amine) | —(CH$_2$)$_3$CH$_3$ | 1.6 × 10$^{-8}$ |
| 48 | (cyclohexanone fused N-methyl lactam) | —(CH$_2$)$_3$CH$_3$ | 5.7 × 10$^{-8}$ |
| 49 | (cyclohexanone fused N-methyl lactam) | —(CH$_2$)$_3$CH$_3$ | 88.0 × 10$^{-8}$ |
| 50 | (cyclopentane fused N-methyl lactam) | —(CH$_2$)$_3$CH$_3$ | 9.9 × 10$^{-8}$ |
| 51 | (bicyclic fused N-methyl lactam) | —(CH$_2$)$_3$CH$_3$ | 15.0 × 10$^{-8}$ |

TABLE IV-continued

[Structure: R⁶-substituted phenyl with N=C(X)-N, C(=O), connected to N-CH₂-biphenyl-tetrazole]

| Ex. No. | R⁶ | X | Angiotensin II Receptor Binding IC₅₀(M) |
|---|---|---|---|
| 52 | cyclooctyl with stereochemistry, O—N—CH₃ | —(CH₂)₃CH₃ | $18.0 \times 10^{-8}$ |
| 53 | cyclopentanone-type with O—N—CH₃ | —(CH₂)₃CH₃ | $7.1 \times 10^{-8}$ |
| 54 | cyclohexanone-type with O—N—CH₃ | —(CH₂)₃CH₃ | $16.0 \times 10^{-8}$ |
| 55 | cyclopentanone-type with O—N—CH₂Ph | —(CH₂)₃CH₃ | $7.8 \times 10^{-8}$ |
| 56 | cyclohexanone-type with O—N—CH₂Ph | —(CH₂)₃CH₃ | $9.4 \times 10^{-8}$ |

TABLE IV-continued

[Structure: R⁶-substituted phenyl with N=C(X)-N, C(=O), connected to N-CH₂-biphenyl-tetrazole]

| Ex. No. | R⁶ | X | Angiotensin II Receptor Binding IC₅₀(M) |
|---|---|---|---|
| 57 | cycloheptanone-type with O—N—CH₂Ph | —(CH₂)₃CH₃ | $18.0 \times 10^{-8}$ |

As can be seen from Table IV, the compounds demonstrate excellent Angiotensin II Receptor Binding activity.

The enzyme renin acts on a blood plasma $\alpha_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

The compounds of this invention inhibit the action of AII. By administering a compound of this invention to a rat, and then challenging with angiotensin II, a blockage of the vasopressor response is realized. The results of this test on representative compounds of this invention are shown in Table II.

AII Challenge

Conscious Male okamoto-Aoki SHR, 16–20 weeks old, weighing approximately 330 g are purchased from Charles River Labs (Wilmington, Mass.). Conscious rats are restrained in a supine position with elastic tape. The area at the base of the tail is locally anesthetized by subcutaneous infiltration with 2% procaine. The ventral caudal artery and vein are isolated, and a cannula made of polyethylene (PE) 10–20 tubing (fused together by heat) is passed into the lower abdominal aorta and vena cava, respectively. The cannula is secured, heparinized (1,000 I.U./ml), sealed and the wound is closed. The animals are placed in plastic restraining cages in an upright position. The cannula is attached to a Statham P23Db pressure transducer, and pulsatile blood pressure is recorded to 10–15 minutes with a Gould Brush recorder. (Chan et al., (Drug Development Res., 18:75–94, 1989). Angiotensin II (human sequence, Sigma Chem. Co., St. Louis, Mo.) of 0.05 and 0.1 ug/kg i.v. is injected into all rats (predosing response). Then a test compound, vehicle or a known angiotensin II antagonist is administered i.v., i.p. or orally to each set of rats. The two doses of angiotensin II are given to each rat again at 30, 60, 90, 120, 180, 240 and 300 minutes post dosing the compound or vehicle. The vasopressor response of angiotensin II is measured for the increase in systolic blood pressure in mmHg. The percentage of antagonism or blockade of the vasopressor response of angiotensin II by a compound is calculated using the vasopressor response (increase in systolic blood pressure) of angiotensin II of each rat predosing the compound as 100%. A compound is considered active if at 30 mg/kg i.v. it antagonized at least 50% of the response.

| | Dose (mg/kg) | AII Dose mcg/kg IV | Min Post Dose | Control Before AII | Response After AII | Change | Average Change | & Inhibition |
|---|---|---|---|---|---|---|---|---|
| ANGIOTENSIN II (AII) VASOPRESSOR RESPONSE | | | | | | | | |
| SPONTANEOUSLY HYPERTENSIVE RATS n = 2 Body Weight(s): 355, 340 grams | | | | | | | | |
| CONTROL | | 0.05 | 0 | 220 | 275 | 55 | 47.5 | |
| | | | | 190 | 230 | 40 | | |
| | | 0.1 | | 215 | 275 | 60 | 50 | |
| | | | | 190 | 230 | 40 | | |
| Ex. No. 18 | 3 I.V. | 0.05 | 30 | 185 | 210 | 25 | 15 | 68 |
| | | | | 230 | 235 | 5 | | |
| | | 0.1 | | 230 | 245 | 15 | 12.5 | 75 |
| | | | | 190 | 200 | 10 | | |
| | | 0.05 | 60 | 220 | 250 | 30 | 22.5 | 53 |
| | | | | 190 | 205 | 15 | | |
| | | 0.1 | | 220 | 250 | 30 | 20 | 60 |
| | | | | 190 | 200 | 10 | | |
| | | 0.05 | 90 | 230 | 260 | 30 | 25 | 47 |
| | | | | 190 | 210 | 20 | | |
| | | 0.1 | | 250 | 280 | 30 | 27.5 | 45 |
| | | | | 190 | 215 | 25 | | |
| | | 0.05 | 120 | 200 | 220 | 20 | 45 | 5 |
| | | | | 190 | 260 | 70 | | |
| | | 0.1 | | 200 | 225 | 25 | 50 | 0 |
| | | | | 190 | 265 | 75 | | |
| | | 0.05 | 180 | 230 | 255 | 25 | 20 | 58 |
| | | | | 180 | 195 | 15 | | |
| | | 0.1 | | 230 | 260 | 30 | 25 | 50 |
| | | | | 220 | 240 | 20 | | |
| SPONTANEOUSLY HYPERTENSIVE RATS n = 2 Body weight(s): 330, 340 grams | | | | | | | | |
| | | 0.05 | 240 | 220 | 240 | 20 | 17.5 | 63 |
| | | | | 185 | 200 | 15 | | |
| | | 0.1 | | 220 | 270 | 50 | 45 | 10 |
| | | | | 180 | 220 | 40 | | |
| | | 0.05 | 300 | 210 | 250 | 40 | 42.5 | 11 |
| | | | | 165 | 210 | 45 | | |
| | | 0.1 | | 230 | 270 | 40 | 27.5 | 45 |
| | | | | 180 | 195 | 15 | | |
| CONTROL | | 0.05 | 0 | 255 | 315 | 60 | 47.5 | |
| | | | | 230 | 265 | 35 | | |
| | | 0.1 | | 260 | 322 | 62 | 57 | |
| Ex. No. 21 | 1 I.V. | 0.05 | 30 | 250 | 270 | 20 | 22.5 | 53 |
| | | | | 200 | 225 | 25 | | |
| | | 0.1 | | 260 | 290 | 30 | 27 | 53 |
| | | | | 220 | 244 | 24 | | |
| | | 0.05 | 60 | 250 | 265 | 15 | 15 | 68 |
| | | | | 220 | 235 | 15 | | |
| | | 0.1 | | 250 | 285 | 35 | 25 | 56 |
| | | | | 225 | 240 | 15 | | |
| | | 0.05 | 90 | 260 | 285 | 25 | 17.5 | 63 |
| | | | | 225 | 235 | 10 | | |
| | | 0.1 | | 255 | 295 | 40 | 27.5 | 52 |
| | | | | 225 | 240 | 15 | | |
| SPONTANEOUSLY HYPERTENSIVE RATS n = 2 Body weight(s): 360, 330 grams | | | | | | | | |
| | | 0.05 | 120 | 255 | 275 | 20 | 17.5 | 63 |
| | | | | 215 | 230 | 15 | | |
| | | 0.1 | | 250 | 270 | 20 | 22.5 | 61 |
| | | | | 220 | 245 | 25 | | |
| | | 0.05 | 180 | 245 | 265 | 20 | 17.5 | 63 |
| | | | | 215 | 230 | 15 | | |
| | | 0.1 | | 240 | 275 | 35 | 30 | 47 |
| | | | | 215 | 240 | 25 | | |
| | | 0.05 | 240 | 240 | 270 | 30 | 27.5 | 42 |
| | | | | 225 | 250 | 25 | | |
| | | 0.1 | | 245 | 270 | 25 | 22.5 | 61 |
| | | | | 225 | 245 | 20 | | |
| | | 0.05 | 300 | 235 | 265 | 30 | 30 | 37 |
| | | | | 215 | 245 | 30 | | |
| | | 0.1 | | 245 | 280 | 35 | 37.5 | 34 |
| | | | | 220 | 260 | 40 | | |
| CONTROL | 0.05 | | 0 | 200 | 245 | 45 | 37.5 | |
| | | | | 180 | 210 | 30 | | |

-continued

ANGIOTENSIN II (AII) VASOPRESSOR RESPONSE

| | Dose (mg/kg) | AII Dose mcg/kg IV | Min Post Dose | Control Before AII | Response After AII | Change | Average Change | & Inhibition |
|---|---|---|---|---|---|---|---|---|
| | | 0.1 | | 205 | 250 | 45 | 42.5 | |
| | | | | 175 | 215 | 40 | | |
| Ex. No. 48 | 3 I.V. | 0.05 | 30 | 200 | 205 | 5 | 2.5 | 93 |
| | | | | 170 | 170 | 0 | | |
| | | 0.1 | | 205 | 210 | 5 | 2.5 | 94 |
| | | | | 160 | 160 | 0 | | |

SPONTANEOUSLY HYPERTENSIVE RATS n = 2 Body weight(s): 360, 330 grams

| | | 0.05 | 60 | 200 | 200 | 0 | 0 | 100 |
|---|---|---|---|---|---|---|---|---|
| | | | | 165 | 165 | 0 | | |
| | | 0.1 | | 195 | 202 | 7 | 6 | 86 |
| | | | | 160 | 165 | 5 | | |
| | | 0.05 | 90 | 190 | 195 | 5 | 5 | 87 |
| | | | | 165 | 170 | 5 | | |
| | | 0.1 | | 190 | 205 | 15 | 10 | 76 |
| | | | | 180 | 185 | 5 | | |
| | | 0.05 | 120 | 210 | 215 | 5 | 4 | 89 |
| | | | | 170 | 173 | 3 | | |
| | | 0.1 | | 205 | 215 | 10 | 7.5 | 82 |
| | | | | 170 | 175 | 5 | | |
| | | 0.05 | 180 | 190 | 205 | 15 | 15 | 60 |
| | | | | 160 | 175 | 15 | | |
| | | 0.1 | | 185 | 215 | 30 | 22.5 | 47 |
| | | | | 170 | 185 | 15 | | |
| | | 0.05 | 240 | 195 | 210 | 15 | 15 | 60 |
| | | | | 170 | 185 | 15 | | |
| | | 0.1 | | 200 | 215 | 15 | 22.5 | 47 |
| | | | | 160 | 190 | 30 | | |
| | | 0.05 | 300 | 185 | 210 | 25 | 20 | 47 |
| | | | | 165 | 180 | 15 | | |
| | | 0.1 | | 200 | 215 | 15 | 27.5 | 35 |
| | | | | 150 | 190 | 40 | | |

SPONTANEOUSLY HYPERTENSIVE RATS n = 2 Body weight(s): 270, 280 grams

| | | | | | | | | |
|---|---|---|---|---|---|---|---|---|
| CONTROL | | 0.05 | 0 | 205 | 242 | 37 | 41 | |
| | | | | 190 | 235 | 45 | | |
| | | 0.1 | | 210 | 255 | 45 | 47.5 | |
| | | | | 190 | 240 | 50 | | |
| Ex. No. 48 | 5 P.O. | 0.05 | 30 | 205 | 210 | 5 | 10 | 76 |
| | | | | 195 | 210 | 15 | | |
| | | 0.1 | | 195 | 210 | 15 | 16 | 66 |
| | | | | 190 | 207 | 17 | | |
| | | 0.05 | 60 | 200 | 205 | 5 | 10 | 76 |
| | | | | 185 | 200 | 15 | | |
| | | 0.1 | | 195 | 205 | 10 | 12.5 | 74 |
| | | | | 185 | 200 | 15 | | |
| | | 0.05 | 90 | 185 | 202 | 17 | 8.5 | 79 |
| | | | | 195 | 195 | 0 | | |
| | | 0.1 | | 190 | 202 | 12 | 7 | 85 |
| | | | | 195 | 197 | 2 | | |
| | | 0.05 | 120 | 205 | 205 | 0 | 4 | 90 |
| | | | | 190 | 198 | 8 | | |
| | | 0.1 | | 207 | 207 | 0 | 5 | 89 |
| | | | | 185 | 195 | 10 | | |
| | | 0.05 | 180 | 185 | 185 | 0 | 7.5 | 82 |
| | | | | 185 | 200 | 15 | | |
| | | 0.1 | 185 | 190 | 5 | 12.5 | 74 | |
| | | | | 180 | 200 | 20 | | |

SPONTANEOUSLY HYPERTENSIVE RATS n = 2 Body weight(s): 280, 290 grams

| | | 0.05 | 240 | 185 | 185 | 0 | 2.5 | 94 |
|---|---|---|---|---|---|---|---|---|
| | | | | 180 | 185 | 5 | | |
| | | 0.1 | | 180 | 190 | 10 | 10 | 79 |
| | | | | 180 | 190 | 10 | | |
| | | 0.05 | 300 | 200 | 205 | 5 | 3 | 93 |
| | | | | 175 | 176 | 1 | | |
| | | 0.1 | | 190 | 200 | 10 | 10 | 79 |
| | | | | 175 | 185 | 10 | | |
| CONTROL | | 0.05 | 0 | 152 | 200 | 48 | 44 | |
| | | | | 190 | 230 | 40 | | |
| | | 0.1 | | 160 | 215 | 55 | 52.5 | |
| | | | | 190 | 240 | 50 | | |
| Ex. No. 48 | 1 I.V. | 0.05 | 30 | 165 | 180 | 15 | 15 | 66 |
| | | | | 195 | 210 | 15 | | |
| | | 0.1 | | 165 | 190 | 25 | 25 | 52 |
| | | | | 190 | 215 | 25 | | |
| | | 0.05 | 60 | 160 | 180 | 20 | 20 | 55 |
| | | | | 190 | 210 | 20 | | |
| | | 0.1 | | 170 | 185 | 15 | 15 | 71 |
| | | | | 195 | 210 | 15 | | |
| | | 0.05 | 90 | 157 | 185 | 28 | 26.5 | 40 |

-continued

| | Dose (mg/kg) | AII Dose mcg/kg IV | Min Post Dose | Control Before AII | Response After AII | Change | Average Change | & Inhibition |
|---|---|---|---|---|---|---|---|---|
| | | | | 190 | 215 | 25 | | |
| | | 0.1 | | 175 | 195 | 20 | 25 | 52 |
| | | | | 195 | 225 | 30 | | |
| SPONTANEOUSLY HYPERTENSIVE RATS n = 2 Body weight(s): 350, 330 grams | | | | | | | | |
| | | 0.05 | 120 | 170 | 195 | 25 | 22.5 | 49 |
| | | | | 195 | 215 | 20 | | |
| | | 0.1 | | 175 | 205 | 30 | 36 | 31 |
| | | | | 183 | 225 | 42 | | |
| | | 0.05 | 180 | 165 | 200 | 35 | 27.5 | 38 |
| | | | | 175 | 195 | 20 | | |
| | | 0.1 | | 175 | 215 | 40 | 32.5 | 38 |
| | | | | 175 | 200 | 25 | | |
| | | 0.05 | 240 | 175 | 215 | 40 | 32.5 | 26 |
| | | | | 175 | 200 | 25 | | |
| | | 0.1 | | 175 | 218 | 43 | 35.5 | 32 |
| | | | | 175 | 203 | 28 | | |
| | | 0.05 | 300 | 170 | 217 | 47 | 36 | 18 |
| | | | | 175 | 200 | 25 | | |
| | | 0.1 | | 172 | 210 | 38 | 36.5 | 30 |
| | | | | 175 | 210 | 35 | | |
| CONTROL | | 0.05 | 0 | 196 | 232 | 36 | 38 | |
| | | | | 195 | 235 | 40 | | |
| | | 0.1 | | 182 | 235 | 53 | 54 | |
| | | | | 170 | 225 | 55 | | |
| Ex. No. 49 | 10 I.V. | 0.05 | 30 | 200 | 200 | 0 | 0 | 100 |
| | | | | 155 | 155 | 0 | | |
| | | 0.1 | | 192 | 205 | 13 | 6.5 | 88 |
| | | | | 160 | 160 | 0 | | |
| | | 0.05 | 60 | 185 | 185 | 0 | 1 | 97 |
| | | | | 175 | 177 | 2 | | |
| | | 0.01 | | 175 | 185 | 10 | 7.5 | 86 |
| | | | | 165 | 170 | 5 | | |
| | | 0.05 | 90 | 170 | 175 | 5 | 5 | 87 |
| | | | | 160 | 165 | 5 | | |
| | | 0.1 | | 170 | 175 | 5 | 7.5 | 86 |
| | | | | 150 | 160 | 10 | | |
| | | 0.05 | 120 | 174 | 180 | 6 | 5.5 | 86 |
| | | | | 175 | 180 | 5 | | |
| | | | | 170 | 180 | 10 | 10 | 81 |
| | | | | 165 | 175 | 10 | | |
| | | 0.05 | 180 | 180 | 190 | 10 | 12.5 | 67 |
| | | | | 165 | 180 | 15 | | |
| | | 0.1 | | 175 | 195 | 20 | 20 | 63 |
| | | | | 170 | 190 | 20 | | |
| SPONTANEOUSLY HYPERTENSIVE RATS n = 2 Body weight(s): 330, 330 grams | | | | | | | | |
| CONTROL | | 0.05 | 0 | 207 | 250 | 43 | 34 | |
| | | | | 205 | 230 | 25 | | |
| | | 0.1 | | 200 | 250 | 50 | 42.5 | |
| | | | | 205 | 250 | 35 | | |
| Ex. No. 49 | 5 P.O. | 0.05 | 30 | 200 | 233 | 33 | 21.5 | 37 |
| | | | | 200 | 210 | 10 | | |
| | | 0.1 | | 203 | 236 | 33 | 26.5 | 38 |
| | | | | 195 | 215 | 20 | | |
| | | 0.05 | 60 | 195 | 215 | 20 | 14 | 59 |
| | | | | 202 | 210 | 8 | | |
| | | 0.1 | | 195 | 235 | 40 | 30 | 29 |
| | | | | 195 | 215 | 20 | | |
| | | 0.05 | 90 | 195 | 210 | 15 | 15 | 56 |
| | | | | 190 | 205 | 15 | | |
| | | 0.1 | | 190 | 205 | 15 | 17.5 | 59 |
| | | | | 200 | 220 | 20 | | |
| | | 0.05 | 120 | 185 | 210 | 25 | 20 | 41 |
| | | | | 190 | 205 | 15 | | |
| | | 0.1 | | 195 | 218 | 23 | 19 | 55 |
| | | | | 195 | 210 | 15 | | |
| | | 0.05 | 180 | 200 | 215 | 15 | 12.5 | 63 |
| | | | | 200 | 210 | 10 | | |
| | | 0.1 | | 195 | 235 | 40 | 27.5 | 35 |
| | | | | 195 | 210 | 15 | | |
| SPONTANEOUSLY HYPERTENSIVE RATS n = 2 Body weight(s): 310, 305 grams | | | | | | | | |
| | | 0.05 | 240 | 200 | 230 | 30 | 22.5 | 34 |
| | | | | 185 | 200 | 15 | | |
| | | 0.1 | | 200 | 235 | 35 | 27 | 36 |
| | | | | 186 | 205 | 19 | | |
| CONTROL | | 0.05 | 0 | 200 | 270 | 70 | 55 | |
| | | | | 240 | 280 | 40 | | |
| | | 0.1 | | 200 | 265 | 65 | 55 | |
| | | | | 235 | 280 | 45 | | |

-continued

| | Dose (mg/kg) | AII Dose mcg/kg IV | Min Post Dose | Control Before AII | Response After AII | Change | Average Change | & Inhibition |
|---|---|---|---|---|---|---|---|---|
| | | ANGIOTENSIN II (AII) VASOPRESSOR RESPONSE | | | | | | |
| Ex. No. 50 | 3 I.V. | 0.05 | 30 | 200 | 235 | 35 | 20 | 64 |
| | | | | 225 | 230 | 5 | | |
| | | 0.1 | | 210 | 235 | 25 | 18.5 | 66 |
| | | | | 218 | 230 | 12 | | |
| | | 0.05 | 60 | 195 | 218 | 23 | 16.5 | 70 |
| | | | | 210 | 220 | 10 | | |
| | | 0.1 | | 200 | 225 | 25 | 19 | 65 |
| | | | | 220 | 233 | 13 | | |
| | | 0.05 | 90 | 190 | 202 | 12 | 11 | 80 |
| | | | | 215 | 225 | 10 | | |
| | | 0.1 | | 190 | 225 | 35 | 26.5 | 52 |
| | | | | 220 | 238 | 18 | | |
| | | 0.05 | 120 | 185 | 207 | 22 | 18.5 | 66 |
| | | | | 210 | 225 | 15 | | |
| | | 0.1 | | 185 | 210 | 25 | 14 | 75 |
| | | | | 210 | 213 | 3 | | |
| | | 0.05 | 180 | 200 | 225 | 25 | 22.5 | 59 |
| | | | | 200 | 220 | 20 | | |
| | | 0.1 | | 190 | 220 | 30 | 17.5 | 68 |
| | | | | 220 | 225 | 5 | | |
| | SPONTANEOUSLY HYPERTENSIVE RATS n = 2 Body weight(s): 315, 370 grams | | | | | | | |
| CONTROL | | 0.05 | 0 | 195 | 235 | 40 | 42.5 | |
| | | | | 185 | 230 | 45 | | |
| | | 0.1 | | 200 | 240 | 40 | 42.5 | |
| | | | | 190 | 235 | 45 | | |
| Ex. No. 50 | 5 P.O. | 0.05 | 30 | 200 | 215 | 15 | 22.5 | 47 |
| | | | | 195 | 225 | 30 | | |
| | | 0.1 | | 198 | 227 | 29 | 32 | 25 |
| | | | | 185 | 220 | 35 | | |
| | | 0.05 | 60 | 205 | 225 | 20 | 22.5 | 47 |
| | | | | 185 | 210 | 25 | | |
| | | 0.1 | | 210 | 228 | 18 | 29 | 32 |
| | | | | 185 | 225 | 40 | | |
| | | 0.05 | 90 | 200 | 230 | 30 | 20 | 53 |
| | | | | 180 | 190 | 10 | | |
| | | 0.1 | | 200 | 230 | 30 | 20.5 | 52 |
| | | | | 185 | 196 | 11 | | |
| | | 0.05 | 120 | 203 | 220 | 17 | 13.5 | 68 |
| | | | | 190 | 200 | 10 | | |
| | | 0.1 | | 205 | 240 | 35 | 22.5 | |
| | | | | 185 | 195 | 10 | | |
| | | 0.05 | 180 | 185 | 220 | 35 | 27.5 | 35 |
| | | | | 160 | 180 | 20 | | |
| | | 0.1 | | 205 | 240 | 35 | 35 | 18 |
| | | | | 160 | 195 | 35 | | |
| | SPONTANEOUSLY HYPERTENSIVE RATS n = 2 Body weight(s): 300, 320 grams | | | | | | | |
| CONTROL | | 0.05 | 0 | 215 | 240 | 25 | 30 | |
| | | | | 200 | 235 | 35 | | |
| | | 0.1 | | 205 | 237 | 32 | 41 | |
| Ex. No. 50 | 1 I.V. | 0.05 | 30 | 190 | 220 | 30 | 25 | 17 |
| | | | | 190 | 210 | 20 | | |
| | | 0.1 | | 185 | 215 | 30 | 25 | 39 |
| | | | | 190 | 210 | 20 | | |
| | | 0.05 | 60 | 190 | 220 | 30 | 25 | 17 |
| | | | | 180 | 200 | 20 | | |
| | | 0.1 | | 185 | 220 | 35 | 30 | 27 |
| | | | | 185 | 210 | 25 | | |
| | | 0.05 | 990 | 190 | 225 | 35 | 24 | 20 |
| | | | | 180 | 193 | 13 | | |
| | | 0.1 | | 190 | 230 | 40 | 37.5 | 9 |
| | | | | 180 | 215 | 35 | | |
| | | 0.05 | 120 | 190 | 225 | 35 | 25 | 17 |
| | | | | 180 | 195 | 15 | | |
| | | 0.1 | | 207 | 240 | 33 | 26.5 | 35 |
| | | | | 180 | 200 | 20 | | |
| | | 0.05 | 180 | 220 | 245 | 25 | 22.5 | 25 |
| | | | | 195 | 215 | 20 | | |
| | | 0.1 | | 225 | 250 | 25 | 27.5 | 33 |
| | | | | 185 | 215 | 30 | | |
| | SPONTANEOUSLY HYPERTENSIVE RATS n = 2 Body weight(s): 340, 340 grams | | | | | | | |
| | | 0.05 | 240 | 185 | 230 | 45 | 32.5 | −8 |
| | | | | 185 | 205 | 20 | | |
| | | 0.1 | | 195 | 250 | 55 | 47.5 | −16 |
| | | | | 175 | 215 | 40 | | |
| | | 0.05 | 300 | 185 | 240 | 55 | 37.5 | −25 |
| | | | | 190 | 210 | 20 | | |
| | | 0.1 | | 191 | 244 | 53 | 45.5 | −11 |
| | | | | 180 | 218 | 38 | | |

-continued

| | Dose (mg/kg) | ANGIOTENSIN II (AII) VASOPRESSOR RESPONSE | | | | | | |
|---|---|---|---|---|---|---|---|---|
| | | AII Dose mcg/kg IV | Min Post Dose | Control Before AII | Response After AII | Change | Average Change | & Inhibition |
| CONTROL | | 0.05 | 0 | 160 | 198 | 38 | 45 | |
| | | | | 170 | 222 | 52 | | |
| | | 0.1 | | 165 | 232 | 67 | 61 | |
| | | | | 185 | 240 | 55 | | |
| Ex. No. 51 | 3 I.V. | 0.05 | 30 | 185 | 185 | 0 | 5 | 89 |
| | | | | 175 | 185 | 10 | | |
| | | 0.1 | | 170 | 183 | 13 | 8 | 87 |
| | | | | 180 | 183 | 3 | | |
| | | 0.05 | 60 | 165 | 195 | 30 | 16.5 | 63 |
| | | | | 170 | 173 | 3 | | |
| | | 0.1 | | 175 | 195 | 20 | 11 | 82 |
| | | | | 175 | 177 | 2 | | |
| | | 0.05 | 90 | 165 | 177 | 12 | 10 | 78 |
| | | | | 175 | 183 | 8 | | |
| | | 0.1 | | 185 | 205 | 20 | 12.5 | 80 |
| | | | | 180 | 185 | 5 | | |
| SPONTANEOUSLY HYPERTENSIVE RATS n = 2 Body weight(s): 300, 290 grams | | | | | | | | |
| | | 0.05 | 120 | 165 | 175 | 10 | 7.5 | 83 |
| | | | | 165 | 170 | 5 | | |
| | | 0.1 | | 165 | 186 | 21 | 15.5 | 75 |
| | | | | 180 | 190 | 10 | | |
| | | 0.05 | 180 | 165 | 180 | 15 | 15 | 67 |
| | | | | 170 | 185 | 15 | | |
| | | 0.1 | | 165 | 190 | 25 | 22.5 | 63 |
| | | | | 165 | 185 | 20 | | |
| CONTROL | | 0.05 | 0 | 220 | 265 | 45 | 37.5 | |
| | | | | 210 | 240 | 30 | | |
| | | 0.1 | | 220 | 265 | 45 | 42.5 | |
| | | | | 200 | 240 | 40 | | |
| Ex. No. 52 | 3 I.V. | 0.05 | 30 | 220 | 225 | 5 | 4 | 89 |
| | | | | 200 | 203 | 3 | | |
| | | 0.1 | | 220 | 230 | 10 | 10 | 76 |
| | | | | 195 | 205 | 10 | | |
| | | 0.05 | 60 | 220 | 225 | 5 | 7.5 | 80 |
| | | | | 190 | 200 | 10 | | |
| | | 0.1 | | 205 | 225 | 20 | 17.5 | 59 |
| | | | | 185 | 200 | 15 | | |
| | | 0.05 | 90 | 200 | 242 | 42 | 28.5 | 24 |
| | | | | 190 | 205 | 15 | | |
| | | 0.1 | | 210 | 240 | 30 | 20 | 53 |
| | | | | 185 | 195 | 10 | | |
| SPONTANEOUSLY HYPERTENSIVE RATS n = 2 Body weight(s): 300, 330 grams | | | | | | | | |
| | | 0.05 | 120 | 225 | 250 | 25 | 14 | 63 |
| | | | | 190 | 193 | 3 | | |
| | | 0.1 | | 225 | 250 | 24 | 17.5 | 59 |
| | | | | 195 | 205 | 10 | | |
| | | 0.05 | 180 | 200 | 230 | 30 | 30 | 20 |
| | | | | 190 | 220 | 30 | | |
| | | 0.1 | | 225 | 265 | 40 | 37.5 | 12 |
| | | | | 190 | 225 | 35 | | |
| | | 0.05 | 240 | 225 | 255 | 30 | 27.5 | 27 |
| | | | | 180 | 205 | 25 | | |
| | | 0.1 | | 235 | 260 | 25 | 22.5 | 47 |
| | | | | 180 | 200 | 20 | | |
| | | 0.05 | 300 | 225 | 250 | 25 | 33 | |
| | | | | 180 | 205 | 25 | | |
| | | 0.1 | | 225 | 260 | 35 | 36 | 15 |
| | | | | 183 | 220 | 37 | | |
| CONTROL | | 0.05 | 0 | 195 | 232 | 37 | 40 | |
| | | | | 192 | 235 | 43 | | |
| | | 0.1 | | 185 | 235 | 50 | 42.5 | |
| | | | | 200 | 235 | 35 | | |
| Ex. No. 53 | 5 P.O. | 0.05 | 30 | 195 | 200 | 5 | 10 | 75 |
| | | | | 195 | 210 | 15 | | |
| | | 0.1 | | 195 | 200 | 5 | 17.5 | 59 |
| | | | | 185 | 215 | 30 | | |
| SPONTANEOUSLY HYPERTENSIVE RATS n = 2 Body weight(s): 300, 330 grams | | | | | | | | |
| | | 0.05 | 60 | 175 | 175 | 0 | 7.5 | 81 |
| | | | | 185 | 200 | 15 | | |
| | | 0.1 | | 175 | 190 | 15 | 20 | 53 |
| | | | | 185 | 210 | 25 | | |
| | | 0.05 | 90 | 170 | 170 | 0 | 5 | 88 |
| | | | | 180 | 190 | 10 | | |
| | | 0.1 | | 170 | 175 | 5 | 10 | 76 |
| | | | | 175 | 190 | 15 | | |
| | | 0.05 | 120 | 165 | 165 | 0 | 1 | 98 |
| | | | | 175 | 185 | 10 | | |
| | | 0.1 | | 165 | 177 | 12 | 11 | 74 |

-continued

| | | ANGIOTENSIN II (AII) VASOPRESSOR RESPONSE | | | | | |
|---|---|---|---|---|---|---|---|
| | Dose (mg/kg) | AII Dose mcg/kg IV | Min Post Dose | Control Before AII | Response After AII | Change | Average Change | & Inhibition |
| | | | | 175 | 185 | 10 | | |
| | | 0.05 | 180 | 165 | 165 | 0 | 1.5 | 96 |
| | | | | 175 | 178 | 3 | | |
| | | 0.1 | | 165 | 170 | 5 | 9 | 79 |
| | | | | 170 | 183 | 13 | | |
| | | 0.05 | 240 | 160 | 170 | 10 | 12.5 | 69 |
| | | | | 160 | 175 | 15 | | |
| | | 0.1 | | 165 | 180 | 15 | 12.5 | 71 |
| | | | | 175 | 185 | 10 | | |
| | | 0.05 | 300 | 155 | 165 | 10 | 6.5 | 84 |
| | | | | 170 | 173 | 3 | | |
| | | 0.1 | | 155 | 175 | 20 | 20 | 53 |
| | | | | 155 | 175 | 20 | | |
| | SPONTANEOUSLY HYPERTENSIVE RATS n = 2 Body weight(s): 340, 335 grams | | | | | | | |
| CONTROL | | 0.05 | 0 | 180 | 218 | 38 | 39 | |
| | | | | 185 | 225 | 40 | | |
| | | 0.1 | | 175 | 225 | 50 | 49 | |
| Ex. No. 53 | 3 I.V. | 0.05 | 30 | 185 | 190 | 5 | 10 | 74 |
| | | | | 185 | 200 | 15 | | |
| | | 0.1 | | 180 | 190 | 10 | 9.5 | 81 |
| | | | | 183 | 192 | 9 | | |
| | | 0.05 | 60 | 175 | 175 | 0 | 0.5 | 99 |
| | | | | 184 | 185 | 1 | | |
| | | 0.1 | | 200 | 200 | 0 | 2.5 | 95 |
| | | | | 200 | 205 | 5 | | |
| | | 0.05 | 90 | 170 | 185 | 15 | 12.5 | 68 |
| | | | | 180 | 190 | 10 | | |
| | | 0.1 | | 180 | 198 | 18 | 16.5 | 66 |
| | | | | 183 | 198 | 15 | | |
| | | 0.05 | 120 | 175 | 190 | 15 | 22.5 | 42 |
| | | | | 180 | 210 | 30 | | |
| | | 0.1 | | 180 | 205 | 25 | 17.5 | 64 |
| | | | | 190 | 200 | 10 | | |
| | | 0.05 | 180 | 185 | 190 | 5 | 9 | 77 |
| | | | | 185 | 198 | 13 | | |
| | | 0.1 | | 195 | 210 | 15 | 17.5 | 64 |
| | | | | 180 | 200 | 20 | | |
| | SPONTANEOUSLY HYPERTENSIVE RATS n = 2 Body weight(s): 330, 380 grams | | | | | | | |
| | | 0.05 | 240 | 175 | 200 | 25 | 25 | 36 |
| | | | | 185 | 210 | 25 | | |
| | | 0.1 | | 175 | 210 | 35 | 27.5 | 44 |
| | | | | 190 | 210 | 20 | | |
| | | 0.05 | 300 | 178 | 198 | 20 | 49 | |
| | | | | 175 | 195 | 20 | | |
| | | 0.1 | | 175 | 205 | 30 | 30 | 39 |
| | | | | 175 | 205 | 30 | | |
| CONTROL | | 0.05 | 0 | 230 | 275 | 45 | 45 | |
| | | | | 240 | 285 | 45 | | |
| | | 0.1 | | 220 | 280 | 60 | 55 | |
| | | | | 240 | 290 | 50 | | |
| Ex. No. 55 | 3 I.V. | 0.05 | 30 | 235 | 235 | 0 | 1.5 | 97 |
| | | | | 235 | 238 | 3 | | |
| | | 0.1 | | 225 | 230 | 5 | 2.5 | 95 |
| | | | | 240 | 240 | 0 | | |
| | | 0.05 | 60 | 230 | 230 | 0 | 0 | 100 |
| | | | | 240 | 240 | 0 | | |
| | | 0.1 | | 225 | 230 | 5 | 2.5 | 95 |
| | | | | 240 | 240 | 0 | | |
| | | 0.05 | 90 | 230 | 235 | 5 | 5 | 89 |
| | | | | 237 | 242 | 5 | | |
| | | 0.1 | | 220 | 225 | 5 | 5 | 91 |
| | | | | 235 | 240 | 5 | | |
| | SPONTANEOUSLY HYPERTENSIVE RATS n = 2 Body weight(s): 330, 345 grams | | | | | | | |
| | | 0.05 | 120 | 225 | 225 | 0 | 1.5 | 97 |
| | | | | 232 | 235 | 3 | | |
| | | 0.1 | | 215 | 222 | 7 | 3.5 | 94 |
| | | | | 235 | 235 | 0 | | |
| | | 0.05 | 180 | 220 | 225 | 5 | 2.5 | |
| | | | | 240 | 240 | 0 | | |
| | | 0.1 | | 215 | 225 | 10 | 12.5 | 77 |
| | | | | 230 | 245 | 15 | | |
| | | 0.05 | 240 | 220 | 225 | 5 | 5 | 89 |
| | | | | 240 | 245 | 5 | | |
| | | 0.1 | | 220 | 230 | 10 | 10 | 82 |
| | | | | 240 | 250 | 10 | | |
| | | 0.05 | 300 | 210 | 230 | 20 | 17.5 | 61 |
| | | | | 225 | 240 | 15 | | |
| | | 0.1 | | 220 | 240 | 20 | 27.5 | 50 |

-continued

ANGIOTENSIN II (AII) VASOPRESSOR RESPONSE

| | Dose (mg/kg) | AII Dose mcg/kg IV | Min Post Dose | Control Before AII | Response After AII | Change | Average Change | & Inhibition |
|---|---|---|---|---|---|---|---|---|
| | | | | 215 | 250 | 35 | | |
| CONTROL | | 0.05 | 0 | 230 | 260 | 30 | 35 | |
| | | | | 200 | 240 | 40 | | |
| | | 0.1 | | 220 | 260 | 40 | 45 | |
| | | | | 200 | 250 | 50 | | |
| Ex. No. 55 | 3 P.O. | 0.05 | 30 | 225 | 240 | 15 | 27.5 | 21 |
| | | | | 195 | 235 | 40 | | |
| | | 0.1 | | 220 | 250 | 30 | 37.5 | 17 |
| | | | | 195 | 240 | 45 | | |
| SPONTANEOUSLY HYPERTENSIVE RATS n = 2 Body weight(s): 310, 330 grams | | | | | | | | |
| | | 0.05 | 60 | 210 | 240 | 30 | 32.5 | 7 |
| | | | | 215 | 250 | 35 | | |
| | | 0.1 | | 215 | 255 | 40 | 40 | 11 |
| | | | | 205 | 245 | 40 | | |
| | | 0.05 | 90 | 205 | 230 | 25 | 30 | 14 |
| | | | | 210 | 245 | 35 | | |
| | | 0.1 | | 215 | 245 | 30 | 37.5 | 17 |
| | | | | 205 | 250 | 45 | | |
| | | 0.05 | 120 | 205 | 220 | 15 | 27.5 | 21 |
| | | | | 205 | 245 | 40 | | |
| | | 0.1 | | 205 | 230 | 25 | 27.5 | 39 |
| | | | | 210 | 240 | 30 | | |
| | | 0.05 | 180 | 205 | 240 | 35 | 30 | 14 |
| | | | | 205 | 230 | 25 | | |
| | | 0.1 | | 210 | 240 | 30 | 32.5 | 28 |
| | | | | 205 | 240 | 35 | | |
| CONTROL | | 0.05 | 0 | 210 | 245 | 35 | 27.5 | |
| | | | | 220 | 240 | 20 | | |
| | | 0.1 | | 220 | 255 | 35 | 31 | |
| | | | | 230 | 257 | 27 | | |
| Ex. No. 56 | 3 P.O. | 0.05 | 30 | 215 | 238 | 23 | 19 | 31 |
| | | | | 215 | 230 | 15 | | |
| | | 0.1 | | 220 | 245 | 25 | 27.5 | 11 |
| | | | | 210 | 240 | 30 | | |
| SPONTANEOUSLY HYPERTENSIVE RATS n = 2 Body weight(s): 300, 310 grams | | | | | | | | |
| | | 0.05 | 60 | 215 | 230 | 15 | 22.5 | 18 |
| | | | | 200 | 230 | 30 | | |
| | | 0.1 | | 210 | 240 | 30 | 25 | 19 |
| | | | | 210 | 230 | 20 | | |
| | | 0.05 | 90 | 205 | 225 | 20 | 17.5 | 36 |
| | | | | 215 | 230 | 15 | | |
| | | 0.1 | | 200 | 230 | 30 | 25 | 19 |
| | | | | 215 | 235 | 20 | | |
| | | 0.05 | 120 | 205 | 230 | 25 | 17.5 | 36 |
| | | | | 210 | 220 | 10 | | |
| | | 0.1 | | 200 | 230 | 30 | 22.5 | 27 |
| | | | | 220 | 235 | 15 | | |
| | | 0.05 | 180 | 195 | 235 | 40 | 30 | −9 |
| | | | | 220 | 240 | 20 | | |
| | | 0.1 | | 200 | 230 | 30 | 30 | 3 |
| | | | | 215 | 245 | 30 | | |
| CONTROL | | 0.05 | 0 | 245 | 280 | 35 | 32.5 | |
| | | | | 225 | 255 | 30 | | |
| | | 0.1 | | 240 | 285 | 45 | 45 | |
| | | | | 220 | 265 | 45 | | |
| Ex. No. 56 | 3 I.V. | 0.05 | 30 | 245 | 245 | 0 | 0 | 100 |
| | | | | 220 | 220 | 0 | | |
| | | 0.1 | | 240 | 240 | 0 | 0 | 100 |
| | | | | 220 | 220 | 0 | | |
| CONTROL | | 0.05 | 60 | 240 | 240 | 0 | 0 | 100 |
| | | | | 190 | 190 | 0 | | |
| | | 0.1 | | 230 | 235 | 5 | 5 | 89 |
| | | | | 185 | 190 | 5 | | |
| | | 0.05 | 90 | 230 | 230 | 0 | 0 | 100 |
| | | | | 190 | 190 | 0 | | |
| | | 0.1 | | 235 | 240 | 5 | 5 | 89 |
| | | | | 180 | 185 | 5 | | |
| | | 0.05 | 120 | 225 | 240 | 15 | 7.5 | 77 |
| | | | | 195 | 195 | 0 | | |
| | | 0.1 | | 235 | 245 | 10 | 10 | 78 |
| | | | | 195 | 205 | 10 | | |
| | | 0.05 | 180 | 225 | 235 | 10 | 7.5 | 77 |
| | | | | 195 | 200 | 5 | | |
| | | 0.1 | | 230 | 242 | 12 | 11 | 76 |
| | | | | 195 | 205 | 10 | | |
| | | 0.05 | 240 | 235 | 245 | 10 | 9 | 72 |
| | | | | 185 | 193 | 8 | | |
| | | 0.1 | | 235 | 260 | 25 | 20 | 56 |

-continued
ANGIOTENSIN II (AII) VASOPRESSOR RESPONSE

| | Dose (mg/kg) | AII Dose mcg/kg IV | Min Post Dose | Control Before AII | Response After AII | Change | Average Change | % Inhibition |
|---|---|---|---|---|---|---|---|---|
| | | | | 195 | 210 | 15 | | |
| | | 0.05 | 300 | 230 | 240 | 10 | 11.5 | 65 |
| | | | | 195 | 208 | 13 | | |
| | | 0.1 | | 240 | 245 | 5 | 15 | 67 |
| | | | | 190 | 215 | 25 | | |
| SPONTANEOUSLY HYPERTENSIVE RATS n = 2 Body weight(s): 320, 320 grams ||||||||||
| CONTROL | | 0.05 | 0 | 220 | 265 | 45 | 35 | |
| | | | | 220 | 245 | 25 | | |
| | | 0.1 | | 215 | 270 | 55 | 40 | |
| | | | | 225 | 250 | 25 | | |
| Ex. No. 57 | 3 I.V. | 0.05 | 30 | 210 | 210 | 0 | 0 | 100 |
| | | | | 220 | 220 | 0 | | |
| | | 0.1 | | 210 | 211 | 1 | 0.5 | 99 |
| | | | | 215 | 215 | 0 | | |
| | | 0.05 | 60 | 230 | 230 | 0 | 0 | 100 |
| | | | | 215 | 215 | 0 | | |
| | | 0.1 | | 220 | 230 | 10 | 5 | 88 |
| | | | | 215 | 215 | 0 | | |
| | | 0.05 | 90 | 230 | 235 | 5 | 2.5 | 93 |
| | | | | 215 | 215 | 0 | | |
| | | 0.1 | | 205 | 225 | 20 | 10 | 75 |
| | | | | 215 | 215 | 0 | | |
| | | 0.05 | 120 | 208 | 215 | 7 | 3.5 | 90 |
| | | | | 210 | 210 | 0 | | |
| | | 0.1 | | 205 | 220 | 15 | 7.5 | 81 |
| | | | | 220 | 220 | 0 | | |
| | | 0.05 | 180 | 195 | 220 | 25 | 13.5 | 61 |
| | | | | 210 | 212 | 2 | | |
| | | 0.1 | | 210 | 230 | 20 | 10 | 75 |
| | | | | 215 | 215 | 0 | | |
| SPONTANEOUSLY HYPERTENSIVE RATS n = 2 Body weight(s): 310, 325 grams ||||||||||
| | | 0.05 | 240 | 230 | 240 | 10 | 8 | 77 |
| | | | | 214 | 220 | 6 | | |
| | | 0.1 | | 220 | 240 | 20 | 17.5 | 56 |
| | | | | 210 | 225 | 15 | | |
| | | 0.05 | 300 | 210 | 225 | 15 | 10 | 71 |
| | | | | 215 | 220 | 5 | | |
| | | 0.1 | | 210 | 235 | 25 | 25 | 38 |
| | | | | 210 | 235 | 25 | | |
| CONTROL | | 0.05 | 0 | 214 | 250 | 36 | 38 | |
| | | | | 215 | 255 | 40 | | |
| | | 0.1 | | 210 | 260 | 50 | 47.5 | |
| | | | | 220 | 265 | 45 | | |
| Ex. No. 57 | 3 P.O. | 0.05 | 30 | 210 | 235 | 25 | 25 | 34 |
| | | | | 210 | 235 | 25 | | |
| | | 0.1 | | 210 | 240 | 30 | 30 | 37 |
| | | | | 210 | 240 | 30 | | |
| | | 0.05 | 60 | 215 | 230 | 15 | 12.5 | 67 |
| | | | | 225 | 235 | 10 | | |
| | | 0.1 | | 210 | 240 | 30 | 22.5 | 53 |
| | | | | 220 | 235 | 15 | | |
| | | 0.05 | 90 | 205 | 220 | 15 | 20 | 47 |
| | | | | 205 | 230 | 25 | | |
| | | 0.1 | | 210 | 230 | 20 | 25 | 47 |
| | | | | 210 | 240 | 30 | | |
| SPONTANEOUSLY HYPERTENSIVE RATS n = 2 Body weight(s): 310, 325 grams ||||||||||
| | | 0.05 | 120 | 210 | 240 | 30 | 22.5 | 41 |
| | | | | 205 | 220 | 15 | | |
| | | 0.1 | | 215 | 240 | 25 | 17.5 | 63 |
| | | | | 210 | 220 | 10 | | |
| | | 0.05 | 180 | 195 | 238 | 43 | 34 | 11 |
| | | | | 215 | 240 | 25 | | |
| | | 0.1 | | 210 | 240 | 30 | 22.5 | 53 |
| | | | | 225 | 240 | 15 | | |

What is claimed is:

1. A quinazolinone compound having the formula:

FORMULA I

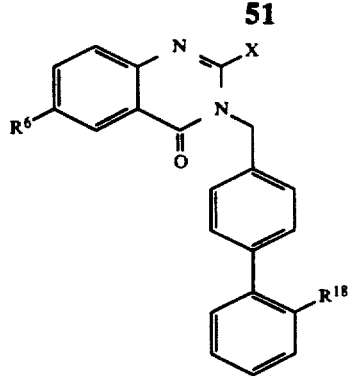

wherein
R^18 is

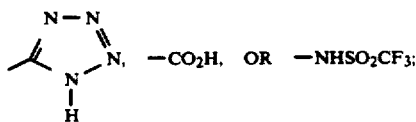, —CO$_2$H, OR —NHSO$_2$CF$_3$;

X is lower alkyl of 3 to 5 carbon atoms;
R$^6$ is:

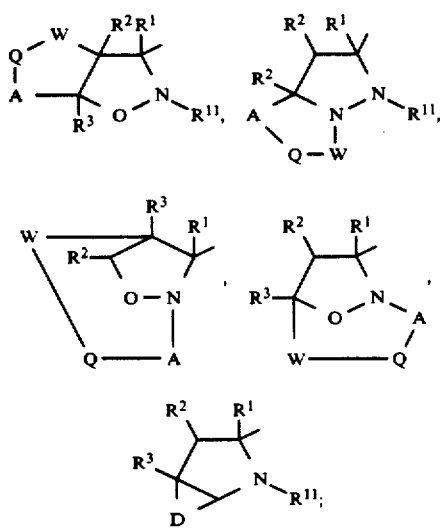

A is —(CH$_2$)$_n$—;
n is 1, 2, 3, or 4;
W is —CH$_2$— or

or A and W are each

and are connected by a —(CH$_2$)$_s$— bridge, wherein
S = 1, 2 or 3;
Q is —O—, —CH$_2$— or

D is —(CH$_2$)$_m$—;
m is 3 or 4;
R$^1$ is H, lower alkyl of 1 to 4 carbon atoms (optionally substituted with —OR$^5$, —CO$_2$R$^5$, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridinyl, thienyl, furyl, —CHO, —CO$_2$R$^5$, —CN,

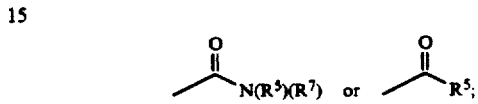

R$^2$ is H, lower alkyl of 1 to 4 carbon atoms (optionally substituted with —OR$_5$, —CO$_2$R$^5$, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridinyl, thienyl, furyl, —CHO, —CO$_2$R$^5$, —CN,

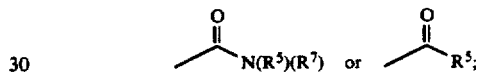

R$^3$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridinyl, thienyl, furyl, —OR$^5$, —N(R$^5$)(R$^7$), —CO$_2$R$^5$, —CH$_2$OR$^5$, —CN, —CHO

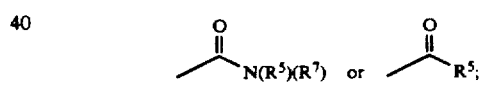

R$^5$ is H, lower alkyl of 1 to 4 carbon atoms;
R$^{11}$ is H, lower alkyl of 1 to 4 carbon atoms, cycloalkyl of 5 or 6 carbon atoms, phenyl, substituted phenyl (substitution selected from mono-lower alkyl of 1 to 3 carbon atoms, trifluoromethyl, nitro, O-alkyl of 1 to 3 carbon atoms, P, Cl, or Br), pyridinyl, thienyl, furyl, benzyl, substituted benzyl (substitution selected from mono-lower alkyl of 1 to 3 carbon atoms, trifluoromethyl, nitro, O-alkyl of 1 to 3 carbon atoms, F, Cl, or Br), —CO$_2$R$^5$, —SO$_2$R$^{10}$,

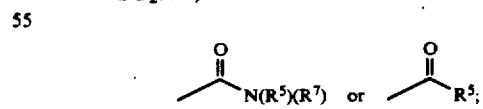

R$^7$ is H, lower alkyl of 1 to 4 carbon atoms;
R$^8$ is H, —CO$_2$R$^5$, —SO$_2$R$^{10}$,

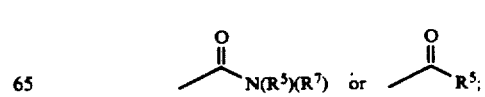

R$^{10}$ is lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br); or pharmaceutically acceptable salts thereof.

2. The compound according to claim 1 wherein the salts are selected from potassium, sodium, calcium, magnesium or ammonium.

3. The compound according to claim 1 wherein

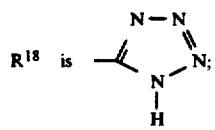

X is a straight chain alkyl of 3 or 4 carbon atoms;

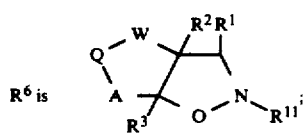

Q is —O— or —CH$_2$—;
R$^1$ is H, lower alkyl of 1 to 4 carbon atoms;
R$^2$ is H, lower alkyl of 1 to 4 carbon atoms;
R$^3$ is H, lower alkyl of 1 to 4 carbon atoms;
R$^{11}$ is H, lower alkyl of 1 to 4 carbon atoms, cyclo alkyl of 5 or 6 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), benzyl or substituted benzyl (substitution selected from mono-lower alkyl of 1 to 3 carbon atoms, trifluoromethyl, nitro, O-alkyl of 1 to 3 carbon atoms, P, Cl, or Br).

4. The compound according to claim 1 wherein

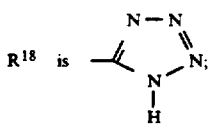

X is a straight chain alkyl of 3 or 4 carbon atoms;

R$^6$ is

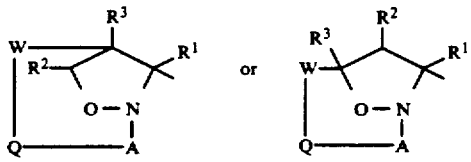

W is —CH$_2$—
Q is —CH$_2$—
R$^1$ is H, lower alkyl of 1 to 4 carbon atoms;
R$^2$ is H, lower alkyl of 1 to 4 carbon atoms;
R$^3$ is H, lower alkyl of 1 to 4 carbon atoms.

5. The compound according to claim 1 wherein

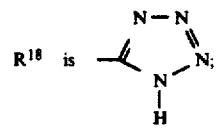

X is a straight chain alkyl of 3 or 4 carbon atoms;

R$^6$ is

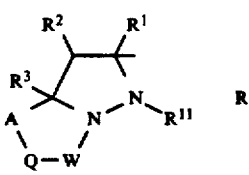 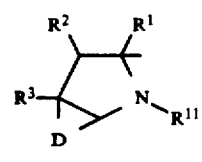

W is —CH$_2$—
Q is —CH$_2$—
R$^1$ is H, lower alkyl of 1 to 4 carbon atoms;
R$^2$ is H, lower alkyl of 1 to 4 carbon atoms;
R$^3$ is H, lower alkyl of 1 to 4 carbon atoms;
R$^{11}$ is H, lower alkyl of 1 to 4 carbon atoms, cyclo alkyl of 5 or 6 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), benzyl or substituted benzyl (substitution selected from mono-lower alkyl of 1 to 3 carbon atoms, trifluoromethyl, nitro, O-alkyl of 1 to 3 carbon atoms, F, Cl, or Br).

6. The compound according to claim 1 wherein
X is a straight chain alkyl of 3 or 4 carbon atoms;
R$^6$ is

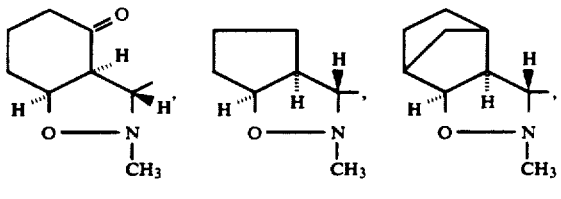

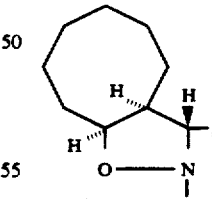 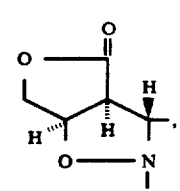 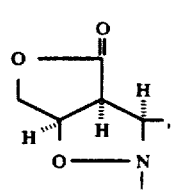

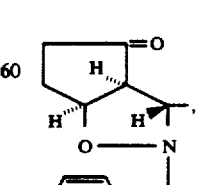 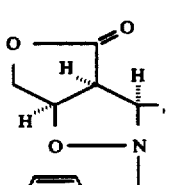 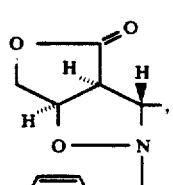

 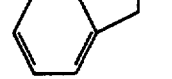 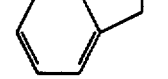

-continued

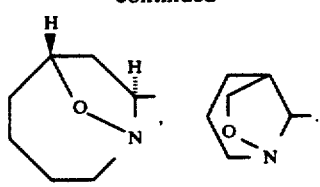

7. A quinazolinone compound having the formula:

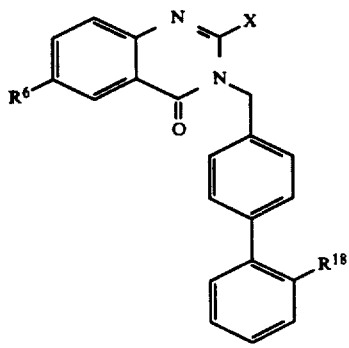

wherein:

$R^{18}$ is

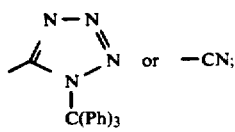  or  —CN;

X is lower alkyl of 3 to 5 carbon atoms;
$R^6$ is:

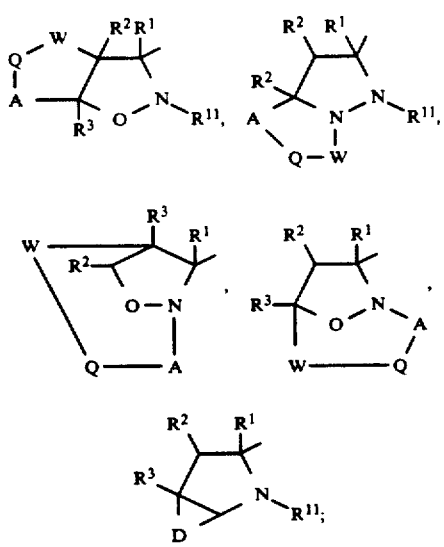

A is —(CH$_2$)$_n$—;
n is 1, 2, 3, or 4;
W is —CH$_2$— or

or A and W are each

and are connected by a —(CH$_2$)$_s$— bridge, wherein S=1, 2 or 3;

Q is —O—, —CH$_2$— or

D is —(CH$_2$)$_m$—;
m is 3 or 4;
$R^1$ is H, lower alkyl of 1 to 4 carbon atoms (optionally substituted with —OR$^5$, —CO$_2$R$^5$, —CN, phenyl, substituted phenyl (substituted selected from mono-lower alkyl of 1 to 3 carbon atoms, trifluoromethyl, nitro, O-alkyl of 1 to 3 carbon atoms, F, Cl, or Br)), pyridinyl, thienyl, furyl, —CHO, —CO$_2$R$^5$, —CN,

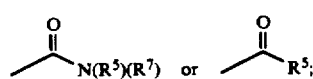

$R^2$ is H, lower alkyl of 1 to 4 carbon atoms, (optionally substituted with —OR$^5$, —CO$_2$R$^5$, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridinyl, thienyl, furyl, —CHO, —CO$_2$R$^5$, —CN,

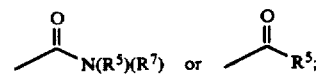

$R^3$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridinyl, thienyl, furyl, —OR$^5$, —N(R$^5$)(R$^7$), —CO$_2$OR$^5$, —CN, —CHO,

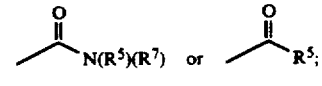

$R^5$ is H, lower alkyl of 1 to 4 carbon atoms;
$R^{11}$ is H, lower alkyl of 1 to 4 carbon atoms, cycloalkyl of 5 or 6 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridinyl, thienyl, furyl, benzyl, substituted benzyl (substitution selected from mono-lower alkyl of 1 to 3 carbon atoms, trifluoromethyl, nitro, O-alkyl of 1 to 3 carbon atoms, F, Cl, or Br), —CO$_2$R$^5$, —SO$_2$R$^{10}$,

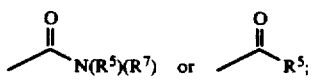

R⁷ is H, lower alkyl of 1 to 4 carbon atoms;
R⁸ is H, —CO₂R⁵, —SO₂R¹⁰,

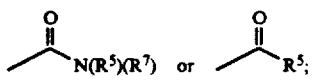

R¹⁰ is lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br).

8. The compound according to claim 7 wherein
X is a straight chain alkyl of 3 or 4 carbon atoms;
R⁶ is

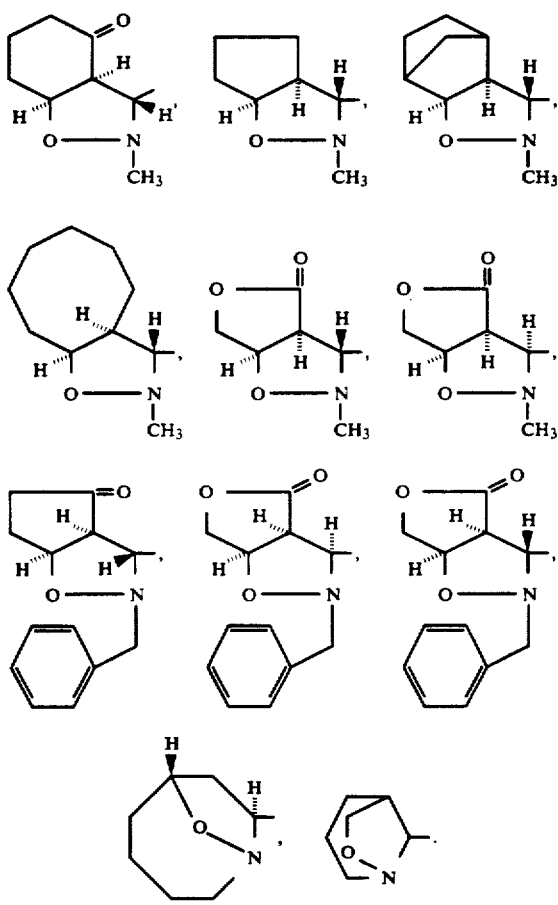

9. The compound according to claim 1 cis-2-Butyl-6-(9-oxa-1-azabicyclo[4.2.1]non-8-yl)-3-[[2'-(1H-tetrazol-5-yl)[1,1'-biphenyl]-4-yl]-methyl]-4(3H)-quinazolinone.

10. The compound according to claim 1 2-Butyl-6-(7-oxa-1-azabicyclo[3.2.1]oct-8-yl)-3-[[2'-(1H-tetrazol-5-yl)[1,1'-biphenyl]-4-yl]-methyl-4(3H)-quinazolinone.

11. The compound according to claim 1 (3α,3aα,6aα)-2-butyl-6- (hexahydro-2-methyl-4-oxo-2H-cyclopent[d]-isoxazol-3-yl)-3-[[2'-(1H)-tetrazol-5-yl)[1,1'-biphenyl]-4-yl]methyl-4(3H)-quinazolinone.

12. The compound according to claim 1 (3α,3aα,7aα)-2-butyl-6-(hexahydro-2-methyl-4-oxo-1,2-benzisoxazol-3-yl)-3-[[2'-(1H-tetrazol-5-yl)-[1,1'-biphenyl]-4-yl]methyl]-4(3H)-quinazolinone.

13. The compound according to claim 1 (3α,3aα,6aα)-2-butyl-6-(hexahydro-2-methyl-2H-cyclopenta[d]isoxazol-3-yl)-3-[[2'-(1H-tetrazol-5-yl)[1,1'-biphenyl]-4-yl]methyl]-4(3H)-quinazolinone.

14. The compound according to claim 1 (3α,3aα,7aα)-2-butyl-6-(octahydro-2-methyl-4,7-methano-1,2-benzisoxazol-3-yl)-3-[[2'-(1H-tetrazol-5-yl)[1,1'-biphenyl]-4-yl]methyl]-4(3H)-quinazolinone.

15. The compound according to claim 1 (3α,3aα,9aα)-2-butyl-6-(decahydro-2-methylcyclooct[d]isoxazol-3-yl)-3-[[2'-(1H-tetrazol-5-yl)[1,1'-biphenyl]-4-yl]methyl]-4(3H)-quinazolinone.

16. The compound according to claim 1 (3α,3aα,6aα)-2-butyl-6-(hexahydro-2-methyl-4-oxofuro[3,4-d]isoxazol-3-yl)-3-[[2'-(1H-tetrazol-5-yl)[1,1'-biphenyl]-4-yl]methyl]-4(3H)-quinazolinone.

17. The compound according to claim 1 (3α,3aα,6aα)-2-butyl-6-[hexahydro-4-oxo-2-(phenylmethyl)2H-cyclopent[d]isoxazol-3-yl]-3-[[2'-(1H-tetrazol-5-yl)[1,1'-biphenyl]-4-yl]methyl]-4(3H)-quinazolinone.

18. The compound according to claim 1 (3α,3aβ,6aβ)-2-butyl-6-[hexahydro-4-oxo-2-(phenylmethyl)furo[3,4-d]isoxazol-3-yl]-3-[[2'-(1H-tetrazol-5-yl)[1,1'-biphenyl]-4-yl]methyl]-4(3H)-quinazolinone.

19. The compound according to claim 1 (3α,3aα,6aα)-2-butyl-6- [hexahydro-4-oxo-2-(phenylmethyl)-furo[3,4-d]isoxazol-3-yl]-3-[[2'-(1H-tetrazol-5-yl)[1,1'-biphenyl]-4-yl]methyl]-4(3H)-quinazolinone.

20. The compound according to claim 7 (3α,3aα,6aα)-2-butyl-6-[hexahydro-2-methyl-4-oxofuro[3,4-d]isoxazol-3-yl]-3-[[2'-[1-(triphenylmethyl)-1H-tetrazol-5-yl][1,1'-biphenyl]-4-yl]methyl]-4(3H)-quinazolinone.

21. The compound according to claim 7 (3α,3aα,6aα)-2-butyl-6-[hexahydro-2-methyl-2H-cyclopent[d]isoxazol-3-yl]-3-[[2'-[1-(triphenylmethyl)-1H-tetrazol-5-yl][1,1'-biphenyl]-4-yl]methyl]-4(3H)-quinazolinone.

22. The compound according to claim 7 (3α,3aα,4β,7β,7aα)-2-butyl-6-(octahydro-2-methyl-4,7-methano-1,2-benzisoxazol-3-yl)-3-[[2'-[1-(triphenylmethyl)-1H-tetrazol-5-yl][1,1'-biphenyl]-4-yl]-methyl]-4(3H)-quinazolinone.

23. The compound according to claim 7 (3α,3aα,7aα)-2-butyl-6-(octahydro-2-methyl-4-oxo-1,2-benzisoxazol-3-yl)-3-[[2'-[1-(triphenylmethyl)-1H-tetrazol-5-yl][1,1'-biphenyl]-4-yl]methyl]-4(3H)-quinazolinone.

24. The compound according to claim 7 (3α,3aα,9aα)-2-butyl-6-(decahydro-2-methylcyclooct[d]isoxazol-3-yl)-3-[[2'-[1-(triphenylmethyl)-1H-tetrazol-5-yl][1,1'-biphenyl]-4-yl]methyl]-4(3H)quinazolinone.

25. The compound according to claim 7 (3α,3aα,6aα) -2-butyl-6-hexahydro-2-methyl-4-oxo-2H-cyclopent[d]isoxazol-3-yl)-3-[[2'-[1-(triphenylmethyl)-1H-tetrazol-5-yl][1,1'-biphenyl]-4-yl]methyl]-4(3H)-quinazolinone.

26. The compound according to claim 7 (3α,3aα,6aα)-2-butyl-6-[hexahydro-4-oxo-2-(phenylmethyl)furo[3,4-d]isoxazol-3-yl]-3-[[2'-[1-(triphenylmethyl)-1H-tetrazol-5-yl][1,1'-biphenyl]-4-yl]methyl]-4(3H)-quinazolinons.

27. The compound according to claim 7 (3α,3aβ,6aβ)-2-butyl-6-[hexahydro-4-oxo-2-(phenylmethyl)furo[3,4-d]isoxazol-3-yl]-3-[[2'-[1-(triphenylmethyl)-1H-tetrazol-5-yl][1,1'-biphenyl]-4-yl]methyl]-4(3H)-quinazolinone.

28. The compound according to claim 7 (3α,3aα,6 aα)-3-[2-butyl-4-[[2'-[1-(triphenylmethyl)-1H-tetrazol-5-yl][1,1'-biphenyl]-4-yl]methoxy]-6-quinazolinyl]hexahydro-2-(phenylmethyl)-4H-cyclopent[d]isoxazol-4-one.

29. A quinazolinone compound having the formula

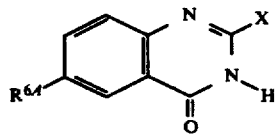

wherein:
X is straight or branched alkyl of 3 to 5 carbon atoms;
R⁶ is:

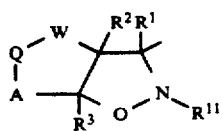

A is —(CH₂)ₙ—;
n is 1, 2, 3, or 4;
W is —CH₂— or

or A and W are each

and are connected by a —(CH₂)ₛ— bridge, wherein S=1, 2 or 3;
Q is —O—, —CH₂— or

R¹ is H, lower alkyl of 1 to 4 carbon atoms (optionally substituted with —OR⁵, —CO₂R⁵, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridinyl, thienyl, furyl, —CHO, —CO₂R⁵, —CN,

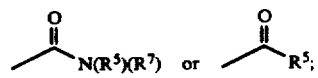

R² is H, lower alkyl of 1 to 4 carbon atoms, (optionally substituted with —OR⁵, —CO₂R⁵, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridinyl, thienyl, furyl, —CHO, —CO₂R⁵, —CN,

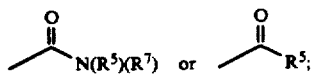

R³ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridinyl, thienyl, furyl, —OR⁵, —N(R⁵)(R⁷), —CO₂R⁵, —CH₂OR⁵, —CN, —CHO,

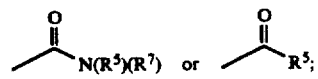

R⁵ is H, lower alkyl of 1 to 4 carbon atoms;
R¹¹ is H, lower alkyl of 1 to 4 carbon atoms, cycloalkyl of 5 or 6 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridinyl, thienyl, furyl, benzyl, substituted benzyl (substitution selected from mono-lower alkyl of 1 to 3 carbon atoms, trifluoromethyl, nitro, O-alkyl of 1 to 3 carbon atoms, F, Cl, or Br), —CO₂R⁵, —SO₂R¹⁰,

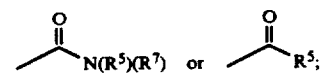

R⁷ is H, lower alkyl of 1 to 4 carbon atoms;
R⁸ is H, —CO₂R⁵, —SO₂R¹⁰,

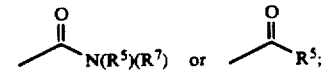

R¹⁰ is lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br).

30. The compound according to claim 29 wherein X is a straight chain alkyl of 3 to 4 carbon atoms;
R⁶⁴ is:

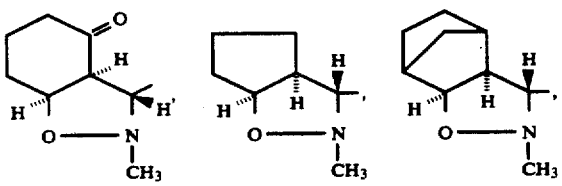

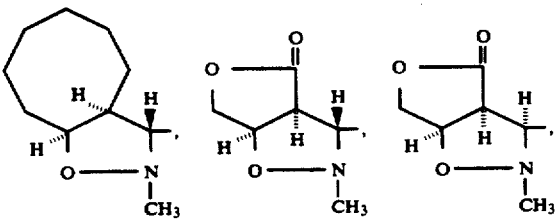

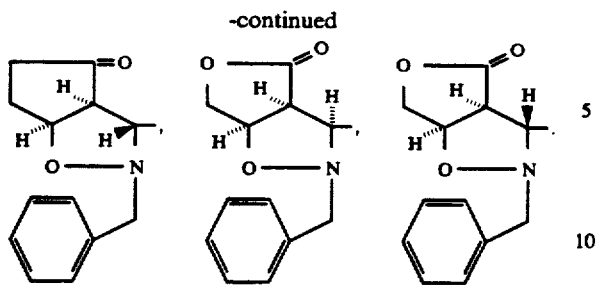

31. The compound according to claim 29 (3α,3aα,-6aα)-2-butyl-6-(hexa-hydro-2-methyl-4-oxo-2H-cyclopent[d]isoxazol-3-yl-4(1H)-quinazolinone.

32. The compound according to claim 29 (3α,3aα,-9aα)-2-butyl-6-(decahydro-2-methylcyclooct[d]isoxazol-3-yl)-4(1H)-quinazolinone.

33. The compound according to claim 29 (3α,3aα,-6aα)-2-butyl-6-(hexahydro-2-methyl-4-oxofuro[3,-4]isoxazol-3-yl)-4(1H)-quinazolinone.

34. The compound according to claim 29 (3α,3aα,-7aα)-2-butyl-6-(octahydro-2-methyl-4,7-methano-1,2-benzisoxazol-3-yl)-4(1H)-quinazolinone.

35. The compound according to claim 29 (3α,3aβ,-7aβ) -2 -butyl-6-(octahydro-2 -methyl-4-oxo-1,2-benzisoxazol-3-yl)-4(1H)-quinazolinone.

36. The compound according to claim 29 (3α,3aα,-6aα)-2-butyl-6-(hexahydro-2-methyl-2H-cyclopent[-d]isoxazol-3-yl)-4(1H)-quinazolinone.

37. The compound according to claim 29 (3α,3aβ,-6aβ) -2-butyl-6-(hexahydro-4-oxo-2-(phenylmethyl)-2H-cyclopent[d]isoxazol-3-yl)-4(1H)-quinazolinone.

38. The compound according to claim 29 (3α,3aα,-6aα) -2-butyl-6-(hexahydro-4-oxo-2-(phenylmethyl)-2H-cyclopent[d]isoxazol-3-yl]-4(1H)-quinazolinone.

39. The compound according to claim 29 (3α,3aβ,-6aβ) -2-butyl-6-(hexahydro-4-oxo-2-(phenylmethyl)-furo[3,4-d]isoxazol-3-yl]-4(1H)-quinazolinone.

40. The compound according to claim 29 (3α,3aα,-6aα) -2-butyl-6-(hexahydro-4-oxo-2-(phenylmethyl)-furo[3,4-d]isoxazol-3-yl]-4(1H)-quinazolinone.

41. A quinazolinone compound having the formula:

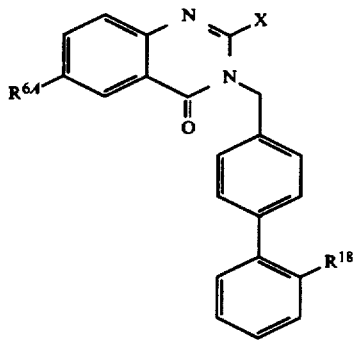

FORMULA I wherein:
$R^{18}$ is —CN or

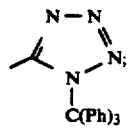

X is straight or branched alkyl of 3 to 5 carbon atoms; $R^{6B}$ is:

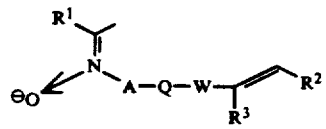

A is —$(CH_2)_n$—;
n is 1, 2, 3 or 4;
W is —$CH_2$— or

or A and W are each

and are connected by a —$(CH_2)_s$— bridge, where s=1, 2 or 3;
Q is —O—, —$CH_2$— or

$R^1$ is H, lower alkyl of 1 to 4 carbon atoms (optionally substituted with —$OR^5$, —$CO_2R^5$, —CN, phenyl, substituted phenyl (substituted selected from mono-lower alkyl of 1 to 3 carbon atoms, trifluoromethyl, nitro, O-alkyl of 1 to 3 carbon atoms, F, Cl, or Br), pyridinyl, thienyl, furyl, —CHO, —$CO_2R^5$, —CN,

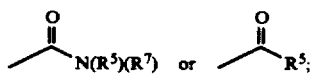

$R^2$ is H, lower alkyl of 1 to 4 carbon atoms, (optionally substituted with —$OR^5$, —$CO_2R^5$, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br)), pyridinyl, thienyl, furyl, —CHO, —$CO_2R^5$, —CN or

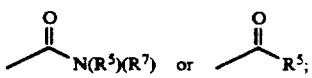

$R^3$ is H, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridinyl, thienyl, furyl, —OR⁵, —N(R⁵)(R⁷), —CO₂R⁵, —CH₂OR⁵, —CN, —CHO,

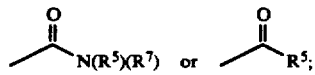

R⁵ is H, lower alkyl of 1 to 4 carbon atoms;
R⁷ is H, lower alkyl of 1 to 4 carbon atoms;
R⁸ is H, —CO₂R⁵, —SO₂R¹⁰,

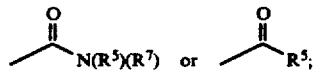

R¹⁰ is lower alkyl of 1 to 4 carbon atoms phenyl, substituted phenyl (substitution selected from mono-lower alkyl of 1 to 3 carbon atoms, trifluoromethyl, nitro, O-alkyl of 1 to 3 carbon atoms, F, Cl or Br).

42. A quinazolinone compound having the formula

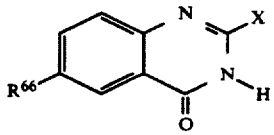

X is straight or branched alkyl of 3 to 5 carbon atoms;
R⁶⁶ is:

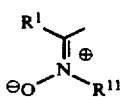

R¹ is H, lower alkyl of 1 to 4 carbon atoms (optionally substituted with —OR⁵, —CO₂R⁵, —CN, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridinyl, thienyl, furyl, —CHO, —CO₂R⁵, —CN

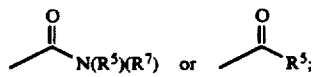

R⁵ is H, lower alkyl of 1 to 4 carbon atoms;
R⁷ is H, lower alkyl of 1 to 4 carbon atoms;
R¹¹ is H, lower alkyl of 1 to 4 carbon atoms, cyclo alkyl of 5 or 6 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl or Br), pyridinyl, thienyl, furyl, benzyl, substituted benzyl (substitution selected from mono-lower alkyl of 1 to 3 carbon atoms, trifluoromethyl, nitro, O-alkyl of 1 to 3 carbon atoms, F, Cl or Br), —CO₂R⁵, —SO₂R¹⁰,

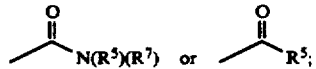

R¹⁰ is lower alkyl of 1 to 4 carbon atoms, phenyl, substituted phenyl (substitution selected from mono-lower alkyl of 1 to 3 carbon atoms, trifluoro methyl, nitro, O-alkyl of 1 to 3 carbon atoms, F, Cl or Br).

43. The compound according to claim 42 2-Butyl-6-[(methylimino)methyl]-4(1H)-quinazolinone N⁶-oxide.

44. The compound according to claim 42 2-Butyl-6-[[(phenylmethyl)imino]methyl]-4(1H)-quinazolinone N⁶-oxide.

45. The compound according to claim 42 2-Butyl-6-[(cyclohexylimino)methyl]-4(1H)-quinazolinone N⁶-oxide.

46. A pharmaceutical composition useful for treating angiotensin induced hypertension or congestive heart failure in a mammal comprising a suitable pharmaceutical carrier and an effective amount of a compound of claim 1.

47. A method of treating angiotensin induced hypertension in a mammal comprising administering a compound of claim 1 to said mannal an amount effective to lower angiotensin induced hypertension.

48. A method of treating congestive heart failure in a mammal comprising administering a compound of claim 1 to said mammal in an amount effective to treat congestive heart failure.

49. A method of antagonizing the effects of Angiotensin II in a mammal comprising administering a compound of claim 1 to said mammal in an amount effective to treat the effects of Angiotensin II.

* * * * *